United States Patent
Sanberg et al.

(10) Patent No.: US 8,784,802 B2
(45) Date of Patent: Jul. 22, 2014

(54) ISCHEMIC TISSUE CELL THERAPY

(75) Inventors: Paul R. Sanberg, Spring Hill, FL (US); Nelson Americo Hossne, Jr., São Paulo (BR); Alison E. Willing, Tampa, FL (US); Adriana Invitti, São Paulo (BR)

(73) Assignees: Cryopraxis Criobiologia Ltda., Rio de Janeiro (BR); Universidade Federal de Sao Paulo—UNIFESP, Sao Paulo (BR); University of South Florida, Tampa, FL (US)

( * ) Notice: Subject to any disclaimer, the term of this patent is extended or adjusted under 35 U.S.C. 154(b) by 248 days.

(21) Appl. No.: 13/063,456

(22) PCT Filed: Sep. 14, 2009

(86) PCT No.: PCT/US2009/056867
§ 371 (c)(1),
(2), (4) Date: Jun. 30, 2011

(87) PCT Pub. No.: WO2010/031006
PCT Pub. Date: Mar. 18, 2010

(65) Prior Publication Data
US 2011/0274674 A1 Nov. 10, 2011

Related U.S. Application Data

(60) Provisional application No. 61/173,807, filed on Apr. 29, 2009, provisional application No. 61/096,727, filed on Sep. 12, 2008.

(51) Int. Cl.
*A61K 35/14* (2006.01)

(52) U.S. Cl.
USPC .................................................. 424/93.7

(58) Field of Classification Search
CPC ..... A61K 35/51; A61K 35/28; C12N 5/0634; C12N 5/0645
See application file for complete search history.

(56) References Cited

U.S. PATENT DOCUMENTS

| | | | |
|---|---|---|---|
| 8,377,692 B2 * | 2/2013 | Fulga et al. | 435/377 |
| 2002/0034501 A1 * | 3/2002 | Pawliuk et al. | 424/93.21 |
| 2005/0202098 A1 | 9/2005 | Mevorach | |
| 2006/0210543 A1 | 9/2006 | Leor et al. | |
| 2007/0105217 A1 | 5/2007 | Pecora et al. | |
| 2008/0057043 A1 * | 3/2008 | Naldini et al. | 424/93.21 |
| 2008/0206196 A1 | 8/2008 | Cao et al. | |

OTHER PUBLICATIONS

Busiek et al, J Biol Chem, May 5, 1992, vol. 267, No. 13, pp. 9087-9092.*
Strauer et al, Circulation, 2002, vol. 106, pp. 1913-1918.*
Hossne, Jr et al, Cell Transplantation, 2009, vol. 18, pp. 1299-1310.*
International Preliminary Report on Patentability received for PCT Patent Application No. PCT/US2009/056867, mailed on Mar. 24, 2011, 9 pages.
Office Action received for Chinese Patent Application No. 200980139421.X, mailed on Oct. 4, 2012, 12 pages (7 pages of English Translation and 5 pages of Chinese Office Action).
Extended European Search Report received for European Patent Application No. 09813763.1, mailed on Nov. 22, 2012, 10 pages.
Office Action received for European Patent Application No. 09813763.1, mailed on Jul. 31, 2013, 4 pages.
Babatz et al., "Large-Scale Immunomagnetic Selection of CD14+ Monocytes to Generate Dendritic Cells for Cancer Immunotherapy: A Phase I Study", Journal of Hematotherapy & Stem Cell Research, vol. 12, 2003, pp. 515-523.
Beeres et al., "Sustained Effect of Autologous Bone Marrow Mononuclear Cell Injection in Patients with Refractory Angina Pectoris and Chronic Myocardial Ischemia: Twelve-Month Follow-Up Results", American Heart Journal, vol. 152, No. 4, Oct. 2006, pp. 684.e11-684.e16.
Kamihata et al., "Implantation of Bone Marrow Mononuclear Cells into Ischemic Myocardium Enhances Collateral Perfusion and Regional Function via Side Supply of Angioblasts, Angiogenic Ligands, and Cytokines", Circulation, vol. 104, Aug. 28, 2001, pp. 1046-1052.
Perin et al., "Improved Exercise Capacity and Ischemia 6 and 12 Months after Transendocardial Injection of Autologous Bone Marrow Mononuclear Cells for Ischemic Cardiomyopathy", Circulation, vol. 110, Sep. 14, 2004, pp. II-213 -II-218.
Yokokura et al., "Influence of Angiogenesis by Implantation of Bone Marrow Mononuclear Cells in the Rat Ischemic Heart", Kurume Medical Journal, vol. 54, No. 3-4, 2007, pp. 77-84.
Zhang et al., "Research on Traumatic Brain Injury in Rats after Transplantation of Human Umbilical Cord Blood Mesenchymal Stem Cells", CMFD, Dec. 15, 2005.

* cited by examiner

*Primary Examiner* — Allison Ford
(74) *Attorney, Agent, or Firm* — Morrison & Foerster LLP

(57) ABSTRACT

The present invention is directed to compositions and methods for treatment of ischemic diseases and conditions, particularly myocardial, CNS/brain and limb ischemia. More particularly, the present invention provides methods of treating disorders by administering monocytes obtained from blood, including umbilical cord blood, peripheral blood, or bone marrow to an individual in need of treatment, wherein the drug is administered to the individual at a time point specifically determined to provide therapeutic efficacy. In one embodiment, the cells are for injection into ischemic myocardium for the treatment of angina.

17 Claims, 8 Drawing Sheets

Monocytes and Macrophage are the Critical Components of Cord Blood in the Treatment of Stroke.

FIGURE 6
Monocytes and Macrophage Present in the Cord Blood are Important for Recovery after Stroke.
A
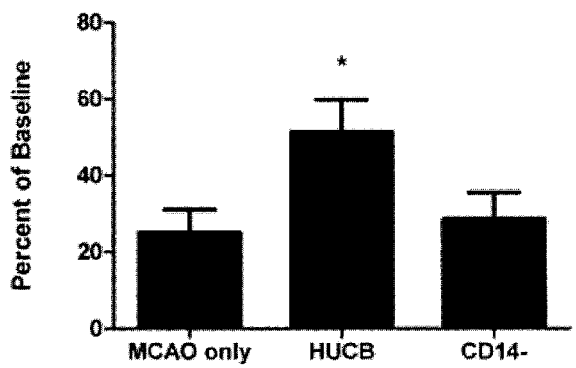
* $p < 0.04$
B
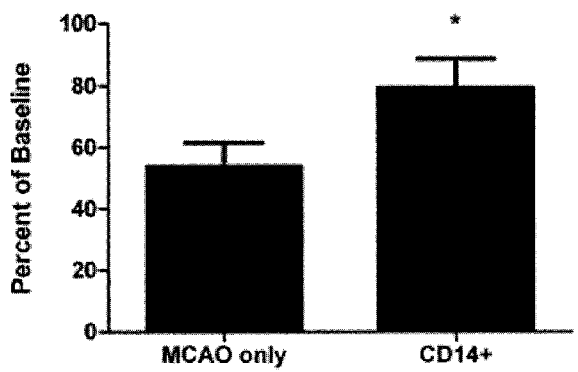
* $p < 0.04$ Monocytes and Macrophage from Cord Blood Reduce Hyperactivity.

US 8,784,802 B2

ISCHEMIC TISSUE CELL THERAPY

STATEMENT OF GOVERNMENT INTEREST

This invention was made with Government support under Grant No. RO1NS52839 awarded by the National Institute of Neurological Disorders and Stroke. The Government has rights in the invention.

CROSS REFERENCE TO RELATED APPLICATIONS

This is a U.S. National Phase patent application of PCT/US2009/056867, filed Sep. 14, 2009, which claims priority to U.S. provisional patent application Ser. No. 61/096,727, filed Sep. 12, 2008, and U.S. provisional patent application Ser. No. 61/173,807, filed Apr. 29, 2009, all of which are hereby incorporated by reference in the present disclosure in their entirety.

FIELD OF THE INVENTION

The present invention relates to the field of treatment of ischemic conditions and diseases, in particular myocardial, brain and limb ischemia, using monocytes isolated from blood. The invention relates to monocyte lineage cell enriched therapeutic cell populations based therapeutics, compositions and methods of manufacture thereof. This invention also relates methods of use of such therapeutics and compositions to treat or prevent ischemia or to otherwise promote tissue perfusion and enhancement of collateral blood vessels formation. In one aspect, a monocyte lineage cell enriched mononucleocyte cell population is used to treat heart ischemia and angina pectoris. In another aspect, the disorder is stroke, and the monocytes are isolated from human umbilical cord blood (HUCB).

BACKGROUND

Angina pectoris is chest pain or discomfort that is caused by insufficient blood flow to the heart muscle. The prevalence of angina in US adults over the age of 20 is estimated at 9,100,000. Stable angina pectoris is angina pectoris where the pain is predictable as occurring upon physical exertion or when the subject is under emotional stress. The prevalence of stable angina in US adults over the age of 45 (without corresponding myocardial infarction) is 500,000. See Rosamond et al. *Circulation* 117(4): e25 (2008).

Current therapies include aspirin, beta blockers (e.g., carvedilol, propranolol, atenolol), nitroglycerin (for acute relief), vasodilators such as calcium channel blockers (e.g., nifedipine (Adalat) and amlodipine), vsosorbide mononitrate and nicorandil, $I_f$ channel inhibitors (e.g., ivabradine), ACE inhibitors, statins, and ranolazine (Ranexa). However, such therapies typically only treat the pain without preventing the pain from recurring and not all angina patients respond to such treatments. Clinical trials are being conducted with CD34 stem cells for treatment of refractory angina with the goal of using the stem cells to generate new vascularization to prevent the pain from recurring. However, this treatment has not yet been demonstrated to be safe and efficacious. Thus, there is a need for a long term treatment option for angina pectoris, particularly refractory angina pectoris.

The management of patients with refractory angina is complex and requires a multidisciplinary approach. Current therapies include aspirin, beta blockers (e.g., carvedilol, propranolol, atenolol), nitroglycerin (for acute relief), vasodilators such as calcium channel blockers (e.g., nifedipine (Adalat) and amlodipine), vsosorbide mononitrate and nicorandil, $I_f$ channel inhibitors (e.g., ivabradine), ACE inhibitors, statins, and ranolazine (Ranexa). And such therapies typically involve exhaustive regimens of trying of numerous different drug regimens and combinations in an attempt to reduce the pain. However, such therapies typically only treat the pain without preventing the pain from recurring and not all angina patients respond to such treatments.

In addition to pharmaceutical therapies, angina may be treated with interventional procedures such as percutaneous transluminal coronary angioplasty or coronary artery bypass graft (CABG) surgery, but such therapies are unavailable to some angina patients due to any number of factors, such as unfavorable coronary anatomy bed, thin coronary arteries, distal or diffuse coronary lesions, etc. Recommendations in the American Heart Association 2002 Guidelines for alternative therapies include surgical laser transmyocardial revascularization (Class IIa), enhanced external counterpulsation and spinal cord stimulation (Class IIb).

New treatment modalities are under investigation including use of stem cell populations. A number of investigators have taken the first steps in demonstrating regeneration of heart tissue using bone marrow mononuclear stem cell containing fractions in the context of myocardial infarction. Such studies have observed: (i) Regeneration of myocardium after infarction; (ii) reduction of infarct size; and (iii) De novo expression of cardiac proteins by human bone marrow cells. Following up on these preliminary studies, several groups have demonstrated the regenerative potential of bone marrow-derived mesenchymal cells in different experimental heart models, with results primarily based upon their myogenic and angiogenic potential.

Clinical trials, mostly in acute myocardial infarction patients and with intracoronary stem cell delivery, have already been undertaken to examine the safety and efficacy of autologous cell transplantation for enhancement of cardiac repair. However, the trials have produced conflicting results without obvious basis in differences in study designs and cell populations or deliveries.

For ischemic heart disease, some clinical trials have demonstrated at least safety of bone marrow-derived mononuclear stem cells with variable degrees of efficacy. The most common delivery technique in these studies is intramyocardial infusion of stem cells—either transendocardial or transepicardial.

In the refractory angina setting, some groups have performed clinical trials mostly using bone marrow mononuclear cells (BMMCs), primarily as a sole treatment or in conjunction with CABG.

By way of example, Hamano et al. injected BMMCs through a transepicardial approach, in conjunction with CABG, in 5 "no option" patients with associated ischemic cardiomyopathy. Results showed an objective increase in myocardial perfusion in the injected area in three patients. However, this study is confounded by the effect of concomitant CABG, and the therapeutic effects of BMMCs treatment remain unclear.

Other investigators have reported their initial experience of endomyocardial injection of BMMCs, delivered with a percutaneous catheter as guided by electromechanical mapping (NOGA™ system). Overall, these nonrandomized studies have demonstrated that direct BMMCs transferred into the ischemic myocardium improved symptoms and exercise capacity and increased myocardial perfusion and function in patients with refractory angina in some but not all patients. Most of these studies enrolled "no option" patients with ischemic cardiomyopathy.

Recently, the first prospective randomized trial of BMMCs by endomyocardial injection in severe coronary disease (PROTECT-CAD) has been reported. This study showed a significant improvement in exercise time, left ventricular ejection fraction and stress-induced myocardial ischemia, in the treated group.

Losordo et al. performed a phase I/IIa, double-blind, randomized, placebo-controlled dose escalating clinical trial with endomyocardial injection of autologous CD34+ stem cells for refractory angina. Efficacy parameters including angina frequency, nitroglycerine usage, exercise time, and CCSAC class showed trends that favored CD34+ cell-treated patients versus control subjects given placebo.

Thus, for "no option" angina patients, clinical studies using bone marrow-derived mononuclear stem cells have shown some myocardial perfusion improvement and, to a lesser degree, improved ventricular function. Most of these studies included patients with ischemic cardiomyopathy, with moderate to severe left ventricular ejection fraction (LVEF) depression. However, to date no therapeutic based upon therapeutic cells (i.e., mononuclear cells or mesodermal stem cells) have been able to reliably reduce the pain or improve the perfusion in most or all patients treated.

Approximately 5 to 15% patients with chronic coronary artery disease present severe disabling angina pectoris which cannot be controlled by a combination of conventional therapy tools, including multiple series of drug therapy optimization treatments, percutaneous transluminal coronary angioplasty (PTCA), and coronary artery bypass grafting (CABG) (35, 37). Severe angina pectoris often results in a substantial decrease in quality of life. Symptom relief for the "no option" refractory angina patient is a complex and challenging process. Alternative therapies in compliance with the American Heart Association Guidelines (11, 14), such as surgical laser transmyocardial revascularization, external counterpulsation, and spinal cord stimulation have all provided modest results at best (9, 26, 31, 45). The vast majority of refractory angina pectoris patients (75%) have preserved left ventricular function, with a mortality rate lower than the general coronary heart disease population (36, 54); and this patient group is rapidly growing.

Cellular therapy, specifically autologous bone marrow cell transplantation, has emerged as a new therapeutic option for cardiac regeneration. Some hypothetical mechanistic explanations involve the stem cells' myogenic and angiogenic potential, and the activation of resident progenitor cell growth via paracrine effects (2, 15-17, 22, 48, 49, 52). Although regeneration of myocardial tissue and concomitant reduction of infarcted area have been demonstrated in experimental animal models, many uncertainties regarding the translation of these results into humans remain (7, 33), rendering BMMC transplantation for cardiac tissue regeneration an experimental procedure, not a standard of care for clinical practice.

On the other hand, refractory angina patients may benefit from cellular based therapy, particularly in regards to angiogenesis. These angiogenic effects are considered among investigators to be very important when cell therapy is considered an option for human patients (8).

Angiogenic effects were reported in several pre-clinical studies (8, 28, 33, 48). The improvement of angiogenesis was observed in hearts transplanted with c-kit bone marrow (BM) cells when compared with negative control mice (40). Mobilization of mouse BM cells into circulation after acute myocardial infarction resulted in regeneration of myocytes and vascular structures (39). A recent study in nonhuman primates using a similar protocol showed an improvement in local perfusion in the BM-treated animals, suggesting potential angiogenic effects (30). This functional benefit in BM cell implantation is likely attributed to a paracrine effect with an increase in angiogenesis through local release of multiple growth factors, such as vascular endothelial growth factor and stromal cell-derived factor-1, among others (8, 48).

In clinical studies involving refractory angina patients, who received bone marrow derived stem cells or BMMC, improvement in symptoms and exercise capacity, as well as in myocardial perfusion were observed (4, 6, 8, 12, 13, 19, 21, 41, 53, 55, 56, 59). Beeres et al. (3) conducted a trial using intramyocardial injection of autologous BMMC in 25 patients with refractory angina, which showed sustained beneficial effects on anginal symptoms and myocardial perfusion. Losordo et al. (34) performed a phase I/IIa, double-blind, randomized, placebo-controlled dose escalating clinical trial with endomyocardial injection of autologous CD34+ stem cells for refractory angina patients, demonstrating a trend of increased exercise time, in addition to Canadian Cardiovascular Society Angina Classification (CCSAC) improvement among CD34+ cell-treated patients. van Ramshorst et al. (58) conducted a randomized controlled trial of intramyocardial bone marrow cell injection for refractory angina, with a short-term follow up (3 to 6 months) showing a modest improvement in myocardial perfusion compared with placebo.

Observing the minimal left ventricular improvement and the clinical response of previous refractory angina trials, it is suggested that the primary action of bone marrow stem cell transplantation in humans is promoting myocardial angiogenesis, and not pure myogenesis. In this setting, angiogenesis can surely improve left ventricular function through rescuing or recruiting hibernating myocardium, but to a limited extent, as demonstrated by these trials and some meta-analysis (1, 32, 44).

Previous pre-clinical and clinical studies have supported the feasibility, safety, and efficacious potential of stem cell therapy for myocardium tissue regeneration and encompasses patients presenting with a range of diagnoses from acute myocardial infarction to chronic ischemic heart disease (33).

The greatest challenge here consists in translating laboratory results to the hospital routine. Differences in study design, stem and mononuclear cell preparation, and infusion techniques have delivered somewhat promising, but inconsistent overall data from different studies (43).

Cerebrovascular disease, considered one of the top five non-communicable diseases, affects approximately 50 million people worldwide, resulting in approximately 5.5 million deaths per year. Of those 50 million, stroke accounts for roughly 40 million people.

Like Angina, Stroke is another condition where ischemia plays a significant role. Stroke is the third leading cause of death in developed countries and accounts for the major cause of adult disability. Presently there is only one available treatment option. It is a vascular disease that impacts cognitive and motor function and alters the immune system. This study focused on the pathophysiology of stroke and the development of a novel cell therapy (human umbilical cord blood (HUCB) cells) that in early studies was shown to significantly improve motor dysfunction and reduce infarct size. The role of the immune/inflammatory response in the development of brain injury after stroke is not fully understood. After the ischemic event, there is an immune response resulting in the influx of neutrophils, T-cells, B-cells, natural killer cells as well as microglia into the infarcted hemisphere and a change in profile of these same immune cells in the peripheral blood. This study examined whether the beneficial effects of HUCB injection can be attributed to a specific cell population.

Stroke treatment consists of two categories: prevention and acute management. Prevention treatments currently consist of antiplatelet agents, anticoagulation agents, surgical therapy, angioplasty, lifestyle adjustments, and medical adjustments. An antiplatelet agent commonly used is aspirin. The use of anticoagulation agents seems to have no statistical significance. Surgical therapy appears to be effective for specific sub-groups. Angioplasty is still an experimental procedure with insufficient data for analysis. Lifestyle adjustments include quitting smoking, regular exercise, regulation of eating, limiting sodium intake, and moderating alcohol consumption. Medical adjustments include medications to lower blood pressure, lowering cholesterol, controlling diabetes, and controlling circulation problems.

Acute management treatments consist of the use of thrombolytics, neuroprotective agents, Oxygenated Fluorocarbon Nutrient Emulsion (OFNE) Therapy, Neuroperfusion, GPIIb/IIIa Platelet Inhibitor Therapy, and Rehabilitation/Physical Therapy.

A thrombolytic agent induces or moderates thrombolysis, and the most commonly used agent is tissue plasminogen activator (t-PA). Recombinant t-PA (rt-PA) helps reestablish cerebral circulation by dissolving (lysing) the clots that obstruct blood flow. It is an effective treatment, with an extremely short therapeutic window; it must be administered within 3 hours from onset. It also requires a CT scan prior to administration of the treatment, further reducing the amount of time available. Genetech Pharmaceuticals manufactures ACTIV ASE® and is currently the only source of rt-P A.

Neuroprotective agents are drugs that minimize the effects of the ischemic cascade, and include, for example, Glutamate Antagonists, Calcium Antagonists, Opiate Antagonists, GAB A-A Agonists, Calpain Inhibitors, Kinase Inhibitors, and Antioxidants. Several different clinical trials for acute ischemic stroke are in progress. Due to their complementary functions of clot-busting and brainprotection, future acute treatment procedures will most likely involve the combination of thrombolytic and neuroprotective therapies. However, like thrombolytics, most neuroprotectives need to be administered within 6 hours after a stroke to be effective.

Oxygenated Fluorocarbon Nutrient Emulsion (OFNE) Therapy delivers oxygen and nutrients to the brain through the cerebral spinal fluid. Neuroperfusion is an experimental procedure in which oxygen-rich blood is rerouted through the brain as a way to minimize the damage of an ischemic stroke. GPIIbIIIa Platelet Inhibitor Therapy inhibits the ability of the glycoprotein GPlIb/IIIa receptors on platelets to aggregate, or clump. Rehabilitational Physical Therapy must begin early after stroke, however, they cannot change the brain damage. The goal of rehabilitation is to improve function so that the stroke survivor can become as independent as possible.

Although some of the acute treatments showed promise in clinical trials, a study conducted in Cleveland showed that only 1.8% of patients presenting with stroke symptoms even received the t-PA treatment (Katz an IL, et ai., 2000 JAMA, 283:1151-1158). t-PA is currently the most widely used of the above-mentioned acute stroke treatments, however, the number of patients receiving any new "effective" acute stroke treatment is estimated to be under 10%. These statistics show a clear need for the availability of acute stroke treatment at greater than 24 hours post stroke.

For some of these acute treatments (Le., t-PA) the time of administration is crucial. Recent studies have found that 42% of stroke patients wait as long as 24 hours before arriving at the hospital, with the average time of arrival being 6 hours after stroke. t-PA has been shown to enhance recovery of −113 of the patients that receive the therapy, however a recent study mandated by the FDA (Standard Treatment with Alteplase to Reverse Stroke found that about a third of the time the three-hour treatment window was violated resulting in an ineffective treatment. With the exception of rehabilitation, the remaining acute treatments are still in clinical trials and are not widely available in the U.S., particularly in rural areas, which may not have large medical centers with the needed neurology specialists and emergency room staffing, access to any of these new methods of stroke diagnosis and therapy may be limited for some time.

The cost of stroke in the US is over $43 billion, including both direct and indirect costs. The direct costs account for about 60% of the total amount and include hospital stays, physicians' fees, and rehabilitation. These costs normally reach $15,000 patient in the first three months; however, in approximately 10% of the cases, the costs are in excess of $35,000. Indirect costs account for the remaining portion and include lost productivity of the stroke victim, and lost productivity of family member caregivers (see National Institute of Neurological Disorders and Stroke, NIH).

Approximately 750,000 strokes occur in the US every year, of which about ⅓ are fatal. Of the remaining patients, approximately ⅓ is impaired mildly, ⅓ is impaired moderately, and ⅓ is impaired severely. Ischemic stroke accounts for 80% of these strokes.

As the baby-boomers age, the total number of strokes is projected to increase substantially. The risk of stroke increases with age. After age 55, the risk of having a stroke doubles every decade, with approximately 40% of individuals in their 80's having strokes. Also, the risk of having a second stroke increases over time. The risk of having a second stroke is 25-40% five years after the first. With the over-65 portion of the population expected to increase as the baby boomers reach their golden years, the size of this market will grow substantially. Also, the demand for an effective treatment will increase dramatically.

Given the inability to effectively mitigate the devastating effects of stroke, it is imperative that novel therapeutic strategies are developed to both minimize the initial neural trauma as well as repair the damage brain once the pathological cascade of stroke has run its course.

Transplantation of monocytes has been proposed as a means of treating stroke. Because of the difficulty in effectively treating patients after stroke, there is a need in the art for methods to enhance the treatment of stroke.

Neovascularization is an integral process of inflammatory reactions and subsequent repair cascades in tissue injury. Monocytes/macrophages play key role in the inflammatory process including angiogenesis as well as the defense mechanisms by exerting microbicidal and immunomodulatory activity. Current studies have demonstrated that recruited monocytes/macrophages aid in regulating angiogenesis in ischemic tissue, tumors, and chronic inflammation. In terms of neovascularization followed by tissue regeneration, monocytes/macrophages should be highly attractive for cell-based therapy compared to any other stem cells due to their considerable advantages such as non-oncogenic, non-teratogenic, no ethical controversy, multiple secretary functions including pro-angiogenic and growth factors, and easy self-harvesting. Not only adult origins such as bone marrow or peripheral blood, but also umbilical cord blood (UCB) can be potential sources for autologous or allogeneic monocytes/macrophages. Especially, UCB monocytes should be considered as the first candidate owing to their fast feasibility, low immune rejection, and multiple skills such as anti-inflammatory reaction in virtue of unique immune and inflammatory immaturity as well as pro-angiogenic ability. General characteristics and potential of monocytes/macrophages are presented for cell-based therapy, especially focusing on neovascularization and UCB-derived monocytes.

One interesting function of monocytes/macrophages is to promote angiogenesis related to inflammatory reactions. Angiogenesis (or neovascularization) is a major element of inflammatory processes including subsequent repair cascades [Sunderkotter, 1994 #4]. During the early inflammatory process, circulating blood monocytes extravasate into tissues [Bosco, 2008 #3]. Initially, neighboring endothelial and inflammatory cells regulate this monocyte passing through vessel wall by releasing of a series of adhesion and chemotactic materials [Baggiolini, 2000 #9; Imhof, 2004 #2; Bosco, 2008 #3]. Along chemotactic and oxygen gradients between normal and injured tissues, extravasated monocytes move and gather into hypoxic and/or necrotic cores of diseased tissues before differentiation into tissue macrophages. The representative pathologic tissues to which monocytes/macrophages are apt to accumulate are as follows: solid tumors, myocardial or cerebral infarction, synovial joints of chronic arthritis or atheromatous plaques, bacterial infection, and healing wounds [Baggiolini, 2000 #9; Murdoch, 2004 #1; Bosco, 2008 #3; Mantovani, 2002 #15] (FIG. 1).

After differentiation from monocytes, macrophages in tissue have been known to exist as polarized populations, M1 and M2 subsets [Mantovani, 2004 #67; Sica, 2006 #16; Mantovani, 2004 #67; Mantovani, 2002 #15]. While M1 polarized macrophages are powerful inflammatory cells that produce pro-inflammatory cytokines and phagocytize pathogens, M2 macrophages modulate the inflammatory responses and help on angiogenesis and tissue repair [Mantovani, 2004 #67; Sica, 2006 #16; Mantovani, 2004 #67; Mantovani, 2002 #15]. Interestingly, in gene expression of macrophages, a combination of M1 and M2 subsets early in wound healing turns into dominantly M2 genes later [Deonarine, 2007 #68]. During the early stage of the wound healing process, M1 macrophages lead to an direct inflammatory reaction that clean up the wound and debris of microbes and/or injured host tissues whereas tissue repair and angiogenesis are begun by M2 macrophages at the same time. In the late stage when the cleansing by M1 macrophages is almost over, the prevailing M2 macrophages go on with their work, tissue regeneration including angiogenesis [Deonarine, 2007 #68]. Accumulating evidence suggests that recruited monocytes/macrophages aid in modulating and regulating neovascularization in ischemic tissue, tumors, and chronic inflammation such as arthritic joints and atherosclerosis.

SUMMARY

The present invention addresses these long felt needs by providing methods and compositions for treatment of ischemia (preferred examples of which are angina and stroke) and for improvement of perfusion that treat the underlying ischemia or need for improved perfusion rather than just treating the pain caused by such conditions and improve the reliability of the efficacy of therapeutic cell based therapeutics for such conditions.

Monocytes, which are derived from monoblasts, hematopoietic stem cell precursors in the bone marrow (BM), circulate in the bloodstream before extravasating into tissues of the body. In the tissues, monocytes differentiate into various types of tissue resident macrophages depending on their anatomical locations, for example, Langerhans cells in skin, Kupffer cells in liver, osteoclasts in bone, microglia in central nervous system, alveolar macrophages in lung, and synovial type A cells in synovial joint (Bosco, et al., 2008, Gordon, 2003, Imhof and Aurrand-Lions, 2004, Murdoch, et al., 2004, Sunderkotter, et al., 1994) (FIG. 1). Monocytes/macrophages can perform phagocytosis by using mediators such as antibodies or complement components that coat the microbes or by binding to the pathogens directly via specific receptors that recognize them (endocytosis). Additionally, monocytes/macrophages are able to kill host cells infected by pathogens, through an immune system response, termed antibody-mediated cellular cytotoxicity (Nathan, 1987, Sunderkotter, et al., 1994). Moreover, they are unique immunoregulatory cells able to both stimulate and suppress immune activities, including antigen presentation to T-cells and controlled secretion of a wide range of cytokines and growth factors (Bosco, et al., 2008, Murdoch, et al., 2004, Paulnock, et al., 2000). In summary, monocytes/macrophages play a major role in the inborn defense system by way of killing pathogens including phagocytosis and cellular cytotoxicity, and immunomodulation (Bosco, et al., 2008, Paulnock, et al., 2000).

Angina and stroke are representative ischemic conditions or condition where a patient is in need of improved perfusion. In that regard, the present invention fulfills in part the need to identify new, unique methods for treating angina, strokes and other forms of ischemia. Other ischemic conditions or conditions where a patient is in need of improved perfusion are in similar need of improved therapies.

In one embodiment, the method comprises administering monocytes to an individual in need of treatment, wherein the monocytes are administered systemically to the individual in an amount and at a time point specifically determined to provide therapeutic efficacy.

An aspect of the invention includes a method of treatment of ischemia in a subject comprising injecting a monocyte lineage cell enriched therapeutic cell population into the ischemic tissue of the subject. In certain embodiments, the ischemia is cardiac ischemia and the ischemic tissue is the myocardium of the heart. Another aspect of the invention includes a method of improving perfusion in a subject comprising injecting a monocyte lineage cell enriched therapeutic cell population into a tissue of the subject in need of improved perfusion. In certain embodiments, the tissue is the myocardium of the heart. Yet another aspect of the present invention is a method of treatment of angina pectoris in a subject comprising injecting a monocyte lineage cell enriched stem cell population into the myocardium of the subject. In embodiments of any of the foregoing aspects, the methods may include injection of at least $10^7$ monocyte lineage cells in the monocyte lineage cell enriched therapeutic cell population. The foregoing aspects and embodiments may further include an embodiment where the monocyte cell population is injected into the myocardium through at least two separate injections, at least three separate injections, at least four separate injections, at least five separate injections, at least ten separate injections, at least twenty separate injections, at least thirty separate injections, at least forty separate injections, at least fifty separate injections, at least sixty separate injections, at least seventy separate injections, at least eighty separate injections, at least ninety separate injections, or at least a hundred separate injections. The foregoing aspects and embodiments may further include an embodiment where an injection is between 0.05 ml and 0.3 ml or is about 0.2 ml. The foregoing aspects and embodiments may further include an embodiment where the monocyte lineage cell enriched therapeutic cell population is autologous or allogeneic to the subject. The foregoing aspects and embodiments may further include an embodiment where the therapeutic cell population is a mononuclear cell population. The foregoing aspects and embodiments may further include an embodiment where prior to the injecting a step selected from the following steps is performed: isolating the stem cells from a sample using a method that enriches monocyte lineage cells; culturing a therapeutic cell population under conditions that enriches monocyte lineage cells; and adding monocyte lineage cells to a therapeutic cell population.

Another aspect of the invention includes an injectable therapeutic comprising a device capable of delivering measured injections of a therapeutic to ischemic tissue wherein the device comprises a reservoir of the therapeutic and the therapeutic comprises a monocyte lineage cell enriched therapeutic cell population. In an embodiment, the therapeutic cell population is a mononuclear cell population. The foregoing aspect and embodiment may further include an embodiment where the monocyte lineage cell enriched therapeutic cell population comprises at least 107 monocyte lineage cells.

SUMMARY OF THE FIGURES

FIG. 6: Step Test measure of motor asymmetry. A) After MCAO, there is a decrease in the number of steps taken with the disabled limb. HUCB administration improves performance of this limb, while recovery is lost by removal of the CD14+ cells (monocytes and macrophage) from the HUCB fraction. B) Injecting only the CD14+ HUCB cells improves motor function of the affected forelimb.

DETAILED DESCRIPTION OF THE PREFERRED EMBODIMENTS

Figure 1:
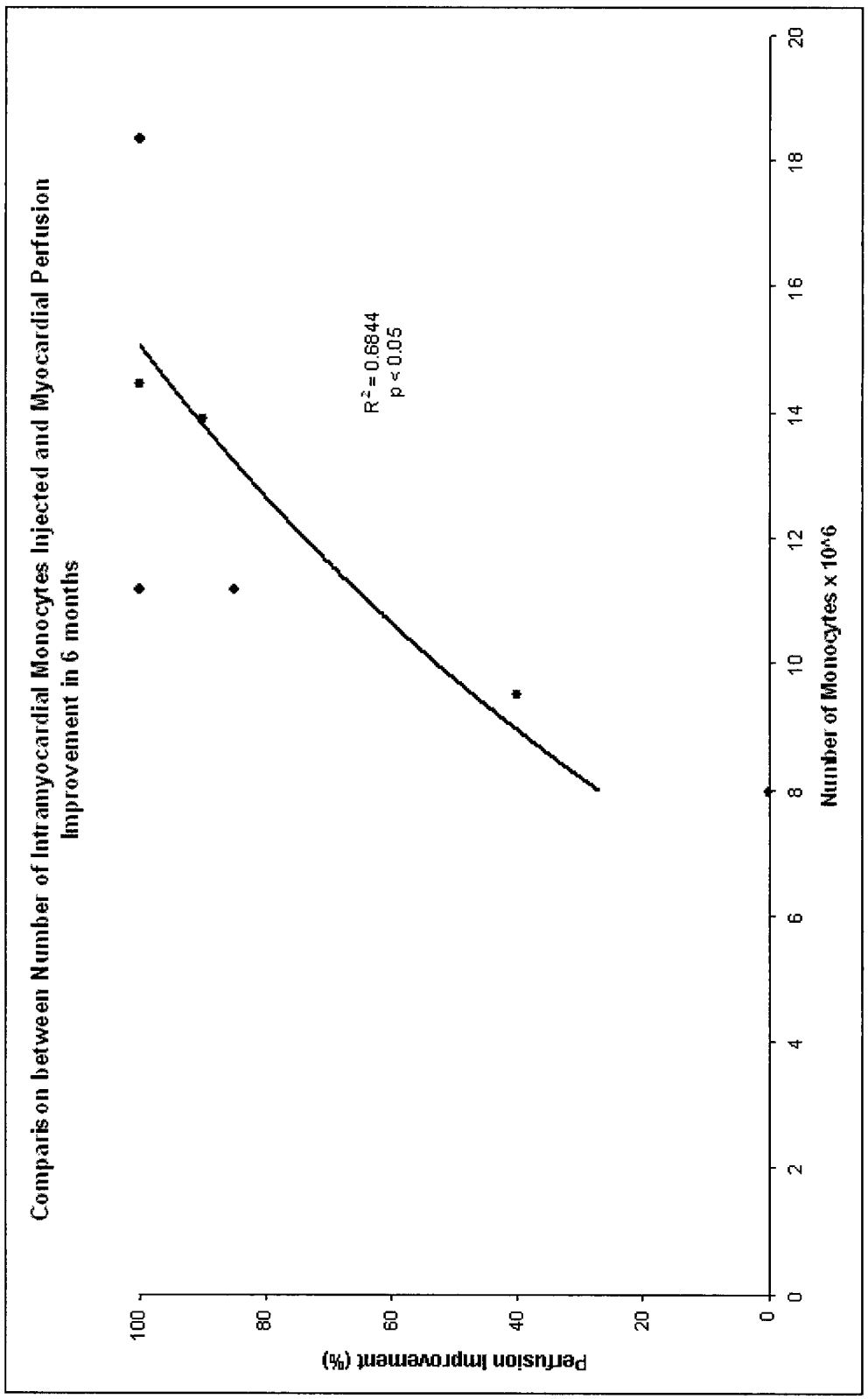
FIG. 1 shows a comparison between the number of intramyocardial monocytes injected (number of cells×10^6, x-axis) and myocardial perfusion improvement (%, y-axis) six months after the cell therapy procedure. The correlation between the number of monocytes injection and myocardial perfusion improvement is illustrated graphically and is statically significant ($p<0.05$, FD=6).

The present invention addresses these long felt needs by providing methods and compositions for treatment of ischemia and for improvement of perfusion generally. A preferred treatment is the treatment of myocardial ischemia and angina. The methods and compositions are dependent in part upon the surprising discovery that enrichment of stem cell populations with monocyte lineage cells improves the reliability of the efficacy observed to date with stem cell based therapeutics.

Bone marrow and bone marrow-derived stem cell populations are a natural source of a broad spectrum of cytokines that are involved in the control of angiogenic and inflammatory processes.

During various stages of angiogenesis, various cytokines are expressed such as tumor necrosis factor-alpha (TNFα), interleukins (ILs), interferon-g (IFN-g), and macrophage colony stimulating factor (MCSF). These cytokines induce smooth muscle cells to express interstitial collagenase and stromelysin, which in turn degrades local collagen resulting in thinning of the blood vessels and their outward bulging.

Cytokines expressed in vessel walls are potent chemoattractants for inflammatory cells induce expression of adhesion molecules on the endothelium and their counterligands on the leukocytes, promote platelet activity and thrombosis, and inhibit thrombolysis.

The bone marrow monocytes or promonocytes can be activated in response to chemotatic stimuli and undergo to final differentiation in macrophages. The macrophages play a key role in angiogenesis through their capacity to secret proteases, growth factors, monokines and the influence in each phase of the angiogenic process such as alterations of local extracellular matrix, induction of endothelial cells to migrate or proliferate and inhibition of vascular growth with formation of differentiated capillaries.

The physiopathological process of the ischemic diseases is the reduction of blood perfusion in certain tissues areas. The cells in the hypoperfusion area suffer lack of sufficient oxygen supply and therefore are unable to perform their natural functions. In this setting, induction of angiogenesis can improve the tissue function through rescuing or recruiting hibernating cells by increasing the supply of oxygen.

The standard refractory angina patient population with viable myocardium and preserved or slightly depressed left ventricular function are ideal candidates for angiogenic therapy employing intramyocardial injection of the monocyte lineage cell enriched stem cell populations of the present invention.

We initiated a nonrandomized clinical trial with refractory angina patients, with preserved or slightly depressed left ventricular function, and intramyocardial injection of BMMC as a sole therapy, in order to enhance myocardial blood flow through angiogenesis, the only well-established outcome of bone marrow stem cell therapy and the unique specific need of this patient population.

Definitions

As used herein, a "therapeutic cell population" can be either or both of a mononuclear cell population and a stem cell population capable of differentiating into cells of mesodermal lineage.

The term "patient" is used herein to describe an animal, preferably a human, to whom treatment, including prophylactic treatment, with the cells according to the present invention, is provided. For treatment of those infections, conditions or disease states which are specific for a specific animal such as a human patient, the term patient refers to that specific animal. The term "donor" is used to describe an individual (animal, including a human) who or which donates umbilical cord blood or umbilical cord blood cells for use in a patient.

The term "umbilical cord blood" is used herein to refer to blood obtained from a neonate or fetus, most preferably a neonate and preferably refers to blood that is obtained from the umbilical cord or the placenta of newborns. Preferably, the umbilical cord blood is isolated from a human newborn. The use of umbilical cord blood as a source of mononuclear cells is advantageous because it can be obtained relatively easily and without trauma to the donor. In contrast, the collection of bone marrow cells from a donor is a traumatic experience. Umbilical cord blood cells can be used for autologous transplantation or allogenic transplantation, when and if needed. Umbilical cord blood is preferably obtained by direct drainage from the cord an/or by needle aspiration from the delivered placenta at the root and at distended veins. As used herein, the term "umbilical cord blood cells" refers to cells that are present within umbilical cord blood. In one embodiment, the umbilical cord blood cells are mononuclear cells that are further isolated from the umbilical cord blood using methods known to those of skill in the art. In a further embodiment, the umbilical cord blood cells may be further differentiated prior to administration to a patient.

The term "effective amount" is used herein to describe concentrations or amounts of components such as differentiation agents, umbilical cord blood cells, precursor or progenitor cells, specialized cells, such as neural and/or neuronal or glial cells, blood brain barrier permeabilizers and/or other agents which are effective for producing an intended result including differentiating stem and/or progenitor cells into specialized cells, such as neural, neuronal and/or glial cells, or treating a neurological disorder or other pathologic condition including damage to the central nervous system of a patient, such as a stroke, heart attack, or accident victim or for effecting a transplantation of those cells within the patient to be treated. Compositions according to the present invention may be used to effect a transplantation of the umbilical cord blood cells within the composition to produce a favorable change in the brain or spinal cord, or in the disease or condition treated, whether that change is an improvement (such as stopping or reversing the degeneration of a disease or condition, reducing a neurological deficit or improving a neurological response) or a complete cure of the disease or condition treated.

The terms "stem cell" or "progenitor cell" are used interchangeably herein to refer to umbilical cord blood-derived stem and progenitor cells. The terms stem cell and progenitor cell are known in the art (e.g., Stem Cells: Scientific Progress and Future Research Directions, report prepared by the National Institutes of Health, June, 2001). The term "neural cells" are cells having at least an indication of neuronal or glial phenotype, such as staining for one or more neuronal or glial markers or which will differentiate into cells exhibiting neuronal or glial markers. Examples of neuronal markers which may be used to identify neuronal cells according to the present invention include, for example, neuron-specific nuclear protein, tyrosine hydroxylase, microtubule associated protein, and calbindin, among others. The term neural cells also includes cells which are neural precursor cells, i.e., stem and/or progenitor cells which will differentiate into or become neural cells or cells which will ultimately exhibit neuronal or glial markers, such term including pluripotent stem and/or progenitor cells which ultimately differentiate into neuronal and/or glial cells. All of the above cells and their progeny are construed as neural cells for the purpose of the present invention. Neural stem cells are cells with the ability to proliferate, exhibit self-maintenance or renewal over the lifetime of the organism and to generate clonally related neural progeny. Neural stem cells give rise to neurons, astrocytes and oligodendrocytes during development and can replace a number of neural cells in the adult brain. Neural stem cells are neural cells for purposes of the present invention. The terms "neural cells" and "neuronal cells" are generally used interchangeably in many aspects of the present invention. Preferred neural cells for use in certain aspects according to the present invention include those cells which exhibit one or more of the neural/neuronal phenotypic markers such as Musashi-1, Nestin, NeuN, class III β-tubulin, GFAP, NF-L, NF-M, microtubule associated protein (MAP2), S100, CNPase, glypican (especially glypican 4), neuronal pentraxin II, neuronal PAS1, neuronal growth associated protein 43, neurite outgrowth extension protein, vimentin, Hu, internexin, O4, myelin basic protein and pleiotrophin, among others.

As used herein, a "stem cell" is a cell from the embryo, fetus, or adult that has, under appropriate conditions, the ability to be cultured for through several divisions without differentiating or dying. Further, a stem cell can, under appropriate conditions, differentiate into at least two distinct cell types.

As used herein, a "pluripotent stem cell" has the ability to differentiate into at least two cell types belong to different germ layer lineages (mesoderm, endoderm, and ectoderm) from which all the cells of the body arise. Pluripotent cells may be obtained from embryos.

An "embryonic stem cell" is a stem cell that was derived from an embryo, typically from the group of cells called the inner cell mass, which is part of the early (4- to 5-day) embryo called the blastocyst. Once removed from the blastocyst the cells of the inner cell mass can be cultured as any other stem cell.

An "adult stem cell" is a stem cell isolated from adult (i.e., non-embryo tissue). Adult stem cells as all stem cells are capable of making identical copies of themselves through numerous rounds of culture. This property is referred to as "self-renewal." Adult stem cells typically generate progenitor or precursor cells under appropriate conditions, which then further differentiate or develop into mature cell types that have characteristic shapes and specialized functions, e.g., cells that form blood vessel walls. Adult stem cells can be isolated from numerous tissues including, by way of example, brain, bone marrow, periosteum, peripheral blood, blood vessels, skeletal muscle, epithelia of the skin and digestive system, cornea, dental pulp of the tooth, retina, liver, pancreas, and adipose tissue.

The term "administration" or "administering" is used throughout the specification to describe the process by which cells of the subject invention, such as umbilical cord blood cells obtained from umbilical cord blood, or more differentiated cells obtained therefrom, are delivered to a patient for therapeutic purposes. Cells of the subject invention be administered a number of ways including, but not limited to, parenteral (such term referring to intravenous and intra-arterial as well as other appropriate parenteral routes), intrathecal, intraventricular, intraparenchymal (including into the spinal cord, brainstem or motor cortex), intracisternal, intracranial, intrastriatal, and intranigral, among others which term allows cells of the subject invention to migrate to the ultimate target site where needed. Cells of the subject invention can be administered in the form of intact umbilical cord blood or a fraction thereof (such term including a mononuclear fraction thereof or a fraction of mononuclear cells, including a high concentration of stem or progenitor cells). The compositions according to the present invention may be used without treatment with a mobilization agent or differentiation agent ("untreated" i.e., without further treatment in order to promote differentiation of cells within the umbilical cord blood sample) or after treatment ("treated") with a differentiation agent or other agent which causes certain stem and/or progenitor cells within the umbilical cord blood sample to differentiate into cells exhibiting a differentiated phenotype, such as a neuronal and/or glial phenotype.

The monocytes can be administered systemically or to a target anatomical site, permitting the cells to differentiate in response to the physiological signals encountered by the cell (e.g., site-specific differentiation). Alternatively, the cells may undergo ex vivo differentiation prior to administration into a patient.

Administration will often depend upon the disease or condition treated and may preferably be via a parenteral route, for example, intravenously, by administration into the cerebral spinal fluid or by direct administration into the affected tissue in the brain. For example, in the case of Alzheimer's disease, Huntington's disease, and Parkinson's disease, the preferred route of administration will be a transplant directly into the striatum (caudate cutamen) or directly into the substantia nigra (Parkinson's disease). In the case of amyotrophic lateral sclerosis (Lou Gehrig's disease) and multiple sclerosis, the preferred administration is through the cerebrospinal fluid. In the case of lysosomal storage disease, the preferred route of administration is via an intravenous route or through the cerebrospinal fluid. In the case of stroke, the preferred route of administration will depend upon where the stroke is, but may be directly into the affected tissue (which may be readily determined using MRI or other imaging techniques), or may be administered systemically. In a preferred embodiment of the present invention, the route of administration for treating an individual post-stroke is systemic, via intravenous or intra-arterial administration.

The terms "grafting" and "transplanting" and "graft" and "transplantation" are used throughout the specification synonymously to describe the process by which cells of the subject invention are delivered to the site where the cells are intended to exhibit a favorable effect, such as repairing damage to a patient's central nervous system (which can reduce a cognitive or behavioral deficit caused by the damage), treating a neurodegenerative disease or treating the effects of nerve damage caused by stroke, cardiovascular disease, a heart attack or physical injury or trauma or genetic damage or environmental insult to the brain and/or spinal cord, caused by, for example, an accident or other activity. Cells of the subject invention can also be delivered in a remote area of the body by any mode of administration as described above, relying on cellular migration to the appropriate area to effect transplantation. Preferably the cells are co-administered with a blood brain barrier permeabilizer.

The term "non-tumorigenic" refers to the fact that the cells do not give rise to a neoplasm or tumor. Stem and/or progenitor cells for use in the present invention are preferably free from neoplasia and cancer.

The term "neurodegenerative disease" is used herein to describe a disease which is caused by damage to the central nervous system and which damage can be reduced and/or alleviated through transplantation of neural cells according to the present invention to damaged areas of the brain and/or spinal cord of the patient. Exemplary neurodegenerative diseases which may be treated using the neural cells and methods according to the present invention include for example, Parkinson's disease, Huntington's disease, amyotrophic lateral sclerosis (Lou Gehrig's disease), Alzheimer's disease, Rett Syndrome, lysosomal storage disease ("white matter disease" or glial/demyelination disease, as described, for example by Folkerth, *J. Neuropath. Exp. Neuro.*, September 1999, 58:9), including Sanfilippo, Gaucher disease, Tay Sachs disease (beta hexosaminidase deficiency), other genetic diseases, multiple sclerosis, brain injury or trauma caused by ischemia, accidents, environmental insult, etc., spinal cord damage, ataxia and alcoholism. In addition, the present invention may be used to reduce and/or eliminate the effects on the central nervous system of a stroke or a heart attack in a patient, which is otherwise caused by lack of blood flow or ischemia to a site in the brain of said patient or which has occurred from physical injury to the brain and/or spinal cord. Neurodegenerative diseases also include neurodevelopmental disorders including for example, autism and related neurological diseases such as schizophrenia, among numerous others.

The term "gene therapy" is used throughout the specification to describe the transfer and stable insertion of new genetic information into cells for the therapeutic treatment of diseases or disorders. The foreign gene is transferred into a cell that proliferates to spread the new gene throughout the cell population. Thus, umbilical cord blood cells, or progenitor cells are the targets of gene transfer either prior to differentiation or after differentiation to a neural cell phenotype. The umbilical cord blood stem or progenitor cells of the present invention can be genetically modified with a heterologous nucleotide sequence and an operably linked promoter that drives expression of the heterologous nucleotide sequence. The nucleotide sequence can encode various proteins or peptides of interest. The gene products produced by the genetically modified cells can be harvested in vitro or the cells can be used as vehicles for in vivo delivery of the gene products (i.e., gene therapy).

Monocyte Lineage Cells

The following written description provides exemplary, but not limiting, methodology and guidance for carrying out many of the varying aspects of the present invention.

The various cells and cell populations discussed throughout may be characterized by a number of methods, including, by way of example, by growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes), gene expression profiling (e.g., gene chip arrays; polymerase chain reaction (for example, reverse transcriptase PCR, real time PCR, and conventional PCR)), protein arrays, protein secretion (e.g., by plasma clotting assay or analysis of PDC-conditioned medium, for example, by Enzyme Linked Immuno-Sorbent Assay (ELISA)), mixed lymphocyte reaction (e.g., as measured by the stimulation of PBMCs), and/or other methods known in the art.

Isolated cells or cell populations may be used to initiate or seed cell cultures for use in the present invention. Such isolated cells or cell populations may be transferred to sterile tissue culture vessels, either uncoated or coated with extracellular matrix or ligands such as laminin, collagen (native, denatured or crosslinked), gelatin, fibronectin, and other extracellular matrix proteins. Cells may be cultured in any culture medium capable of sustaining growth of the cells. Examples of such media (which one of skill in the art may select as appropriate to the type of cell or cell population together with any other media available to one of skill in the art), DMEM (high or low glucose), advanced DMEM, DMEM/MCDB 201, Eagle's basal medium, Ham's F10 medium (F10), Ham's F-12 medium (F12), Iscove's modified Dulbecco's-17 medium, Mesenchymal Stem Cell Growth Medium (MSCGM), DMEM/F12, RPMI 1640, and CELL-GRO-FREE. The culture medium may be supplemented with one or more components as appropriate to the cells or cell populations, including, for example, fetal bovine serum (FBS); equine serum (ES); human serum (HS); beta-mercaptoethanol (BME or 2-ME); one or more growth factors (for example, platelet-derived growth factor (PDGF), epidermal growth factor (EGF), fibroblast growth factor (FGF), vascular endothelial growth factor (VEGF), insulin-like growth factor-1 (IGF-1), leukocyte inhibitory factor (LIF) and erythropoietin (EPO)); amino acids, including L-glutamine and L-valine; and one or more antibiotic and/or antimycotic agents to control microbial contamination (such as, for example, penicillin G. streptomycin sulfate, amphotericin B. gentamicin, and nystatin, either alone or in combination). The cells may be seeded in culture vessels at a density to allow cell expansion.

Methods for the selection of the most appropriate culture medium, medium preparation, and cell culture techniques based upon the type of cells or cell populations are well known in the art and are described in a variety of sources, including Doyle et al., (eds.), 1995, CELL &TISSUE CULTURE: LABORATORY PROCEDURES, John Wiley & Sons, Chichester; and Ho and Wang (eds.), 1991, ANIMAL CELL BIOREACTORS, Butterworth-Heinemann, Boston.

Cells and cell populations suitable for use in the present invention may be expanded by culturing in a defined growth media containing at least one factor that stimulates the proliferation of the cells (appropriate for the applicable cells or cell populations). The at least one factor may include, for example, nicotinamide, members of the TGF-β family, including TGF-β 1, 2, and 3, bone morphogenic proteins (BMP-2, -4, 6, -7, -11, -12, and -13), serum albumin, members of the fibroblast growth factor family, platelet-derived growth factor-AA, and -BB, platelet rich plasma, insulin growth factor (IGF-I, -II) growth differentiation factor (GDF-5, -6, -8, -10, 11), glucagon like peptide-I and -II (GLP-I and -II), GLP-I and GLP-II mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as triethylene pentamine, forskolin, sodium butyrate, activin, betacellulin, noggin, neuron growth factor, nodal, insulin/transferrin/selenium (ITS), hepatocyte growth factor (HGF), keratinocyte growth factor (KGF), bovine pituitary extract, islet neogenesis-associated protein (INGAP), proteasome inhibitors, notch pathway inhibitors, sonic hedgehog inhibitors, or combinations thereof. Alternatively, cells suitable for use in the present invention may be expanded by culturing in conditioned media (i.e., defined cell culture media in which a population of cells was grown to allow the cells to contribute soluble factors to the medium so that the conditioned media includes appropriate soluble factors for the cells or cell populations of interest). In certain embodiments, the cells are removed from the medium while the soluble factors the cells produce remain. This medium can then be used to support different cells or cell populations.

During hematopoiesis along the monocyte lineage, the hematopoietic stem cell first differentiate into a common myeloid progenitor and then into a myeloblast. After the myeloblast, the cell then differentiates into a monoblast. The monoblast is the first cell that is properly part of the monocyte lineage cells as it is committed to differentiation into a monocyte. The monoblast differentiates into a promonocyte. The promonocyte then differentiates into the monocyte. The monocyte can then undergo monocytopoiesis into either a macrophage or a myeloid dendritic cell. Monocyte lineage cells therefore include all cell types beginning with the monoblast all the way through monocytopoiesis.

Monoblasts are readily identifiable to one of skill in the art. Monoblasts are typically between twelve and twenty microns in diameter. The relative volume the nucleus to the cytoplasm is 4:1 to 3:1, and, like most myeloid blasts, has a round to oval nucleus with fine chromatin structure. One to four nucleoli are usually visible. The nucleus can be central or eccentric and it can show evidence of indentation or folding. The cytoplasm is agranular, stains moderately to lightly basophilic, and often has an intensely stained periphery and a prominent perinuclear zone.

Monocytes are similarly readily identifiable to one of skill in the art. Monoblasts are typically between thirteen and twenty-five microns in diameter. Monocytes are large, circulating, phagocytic white bloods cell that have a single large, smooth, well-defined nucleus that is ovoid or kidney-shaped. The large area of cytoplasm has many internal vesicles for processing foreign material and includes fine, azurophilic cytoplasmic granules. Monocytes typically circulate in the bloodstream for about one to three days and then move into other tissues throughout the body such as the lung and liver. After migrating into other tissues, the monocytes undergo monocytopoiesis into different types of macrophages depending upon the type of tissue that the monocyte moves into. Promonocytes are similar to monocytes, but nucleus of the promonocyte is more regular than that of the mature monocyte and the ratio of nucleus to cytoplasm is higher.

Monocyte lineage cells may be isolated from numerous sources using any method available to one of skill in the art. Examples include bone marrow, peripheral blood and cord blood. In addition to obtaining monocyte lineage cells by isolating directly from a subject, monocyte lineage cells may be obtained by differentiation of stem cells including, without limitation, hematopoietic stem cells.

Mononuclear Cell Populations

Mononuclear cell populations may be isolated from numerous sources. One example is by density gradient (varying from 1.0 g/L to 1.1 g/L, preferably 1.077 g/L) as demonstrated in the Examples below. Other examples include bone marrow, peripheral blood and cord blood. In addition to obtaining mononuclear cells by isolating directly from a subject, mononuclear cells may be obtained by differentiation of stem cells including, without limitation, hematopoietic stem cells.

Stem Cell Populations

Stem cell populations suitable for use in the methods of the present invention may be obtained from any tissues that can provide stem cells capable of differentiation into at least cell types of mesodermal lineage.

Bone-marrow derived stem cells are the two most-studied types of adult stem cells. Currently, such bone-marrow derived stem cells are used in the clinic to restore various blood and immune components to the bone marrow via transplantation. There are currently identified two major types of stem cells found in bone marrow: hematopoietic stem cells (HSC, or CD34+ cells) are capable of differentiating into all types of blood and immune cells, and stromal (mesenchymal) stem cells (MSC) that are typically considered to form bone, cartilage, muscle and fat. However, both types of marrow-derived stem cells have been demonstrated to have more extensive plasticity that previously thought.

One of skill in the art may use any means for isolating and culturing stem cells as there are several methods for such that are well known. By way of example, hematopoietic stem cells may be obtained from umbilical cord blood which has an abundant supply of such cells. Hematopoietic stem cells isolated from umbilical cord blood and hematopoietic stem cells isolated from bone marrow or peripheral blood behave essentially identically when used for transplantation. In addition, the placenta and bone marrow are excellent sources for mesenchymal stem cells. Similarly, stem cells that can differentiate into mesodermal lineage cells have been derived from adipose tissue (though apparently not quite as plastic as bone-marrow derived mesenchymal stem cells) and similar stem cells are likely present in other tissues.

Stem cells may also be isolated from many tissues either by use of antibodies that bind markers that are specific to the stem cells (e.g., SH2, SH3, and SH4—see, U.S. Pat. Nos. 5,486,359 and 5,837,539) or by use of antibodies which bind markers specific to the unwanted cells, such as CD4+ and CD8+ (T cells), CD45+ (panB cells), GR-1 (granulocytes), and lad (differentiated antigen presenting cells). An example of this protocol may be found in Izaba et al., I. Exp. Med. 176-1693 1702 (1992).

Hematopoietic stem cells can similarly be obtained from a variety of sources including cord blood, bone marrow, and mobilized peripheral blood. Purification of hematopoietic stem cells can be accomplished by antibody affinity procedures (e.g., use of antibodies to bind CD34 which is specific to hematopoietic cells). An affinity column isolation procedure for isolating cells with such antibodies may be found in Ho et al., Stem Cells 13 (suppl. 31: 100-105 (1995). See also, Brenner, Journal of Hematotherapy 2: 7-17 (1993). Methods for affinity purification and cultural expansion of mesenchymal stem cells are also well known (see, e.g., U.S. Pat. Nos. 5,486,359 and 5,837,539). Additional examples of such isolation methods are taught in U.S. Pat. No. 6,087,113, U.S. Pat. No. 6,261,549, U.S. Pat. No. 5,914,262, U.S. Pat. No. 5,908,782, and US20040058412.

Monocyte Lineage Cell Enriched Therapeutic Cell Populations

The therapeutic cell populations may be enriched by any method available to one of skill in the art. One example includes isolation of the stem cell populations and then selection of those populations that are enriched in monocytes as a result of the isolation. This method is in essence demonstrated in the Examples below, except that the enrichment was determined after use of the mononuclear cell population. The Examples can be readily modified so that the enrichment of the monocytes is measured prior to use and then selecting those populations that have sufficient enrichment and/or subjecting those populations to further enrichment. Since the stem cell populations and mononuclear cell populations include cells that can be induced to differentiate into monocyte lineage cells, one method of enrichment includes addition of one or more appropriate factors to induce such differentiation (which are known to one of skill in the art) to the cell population. Other examples of enrichment include addition or one or more cytokines or other growth factors that promote induce monocyte lineage cells to divide or grow more rapidly than the non-monocyte lineage cells in the cell population and/or addition of one or more factors that selectively inhibit division or growth of cells that are not monocyte lineage cells. Finally, monocyte lineage cells obtained or cultured separately can be added to the therapeutic cell population.

EXAMPLES

The following examples demonstrate representative uses of the methods and compositions disclosed in this specification.

Example 1

Isolation of the Monocyte Lineage Cell Enriched Mononucleocyte Cell Population

The bone marrow mononucleocyte cell preparation was performed by standard density gradient (varying from 1.0 g/L to 1.1 g/L, preferably 1.077 g/L). The cell preparations as discussed in Example 2 below had different amounts of monocyte lineage cells.

The BMMC preparation was performed by density gradient separation with Ficoll Paque PREMIUM® (GE Healthcare). Bone marrow blood, 35 mL, was carefully added in 10 mL Ficoll per tube, without mixture, maintaining intact Ficoll surface tension. This procedure was repeated in 9 tubes, with for a total of 10 tubes/patient. The tubes were than centrifuged at 350 g—without brake, for 40 minutes, at 20° C. After density separation, the mononuclear ring (plasma/ficoll interface) was carefully collected from the 10 tubes and suspended in 4 tubes, with 0.9% saline solution added to result in 45 mL total tube volume. The 4 tubes were centrifuged at 400 g, for 10 minutes, at 20° C., to separate the cells from residual Ficoll. After discarding the supernatant, the mononuclear cells from all tubes were harvested and combined in a single tube with a total volume 40 mL of 0.9% saline solution. The mononuclear cells solution was again centrifuged at 400 g, for 10 minutes, at 20° C. The supernatant was again discarded and the cell pellet was suspended in 10 mL of 0.9% saline solution. Once cells passed lot-release criteria including sterility, viability, and absence of endotoxins, following good manipulation practices (GMPs); and appropriate automatic cell counting performed, the cells were suspended in 0.9% saline plus 20% autologous serum to maintain cell viability (the autologous serum was previously filtered with a 0.22 μm filter to eliminate contaminating cells)—at $1\times10^7$ cells/mL final concentration. The final mononuclear solution was passed through a 100 μm filter to eliminate cell grouping.

Example 2

Correlation Between Number of Monocytes Injected Versus Therapeutic Outcome

The Example that follows presents data from patients treated using the methods and compositions set forth herein.

The aim of our study was to evaluate the safety and efficacy of a proprietarily designed protocol, the Refractory Angina Cell Therapy Protocol (ReACT), in which a single series of multiple intramyocardial injections of a specific BMMC formulation is performed as the sole surgical therapy for these patients.

ReACT was designed in compliance with Good Manufacturing Practices (GMP) and FDA standards criteria.

Patients enrolled in this protocol were required to have refractory angina pectoris, viable myocardium (diagnosed through stress tecnecium scintigraphy), without left ventricular dysfunction (ejection fraction of at least 45%) and not suitable for myocardial revascularization (either PTCA or CABG).

Eight refractory angina patients were included in the study from September 2005 to July 2007. All patients had previously undergone surgical revascularization once (4 patients), twice (3 patients) or four (1 patient) times, without angina relief. Patients' baseline characteristics are described on Table 1.

An additional four refractory angina patients were enrolled and underwent the ReACT, but required simultaneous coronary artery bypass grafting and were excluded from this analysis. These patients are currently being followed as a separate group.

Refractory angina patients routinely attending the São Paulo Hospital, in Sao Paulo, Sao Paulo, Brazil, a referral tertiary Federal University Hospital for coronary heart disease, were included in the study. The study protocol (ReACT) was approved by our local and national ethical committee (CEP-EPM-0314/05), and all patients provided written informed consent. Refractory angina patients were defined as those with functional class IV (angina at rest) according to the Canadian Cardiovascular Society Angina Classification (CCSAC) despite maximum medical therapy, not suitable for conventional myocardial revascularization and with viable myocardium identification. Ineligibility for revascularization—either percutaneous or surgical—was determined by at least 2 cardiologists and 2 cardiovascular surgeons based on the most recent (within 6 months) patient's coronary angiogram. Exclusion criteria were: (1) left ventricular ejection fraction (LVEF)<45% on transthoracic echocardiogram; (2) absence of viable myocardium on cardiac nuclear imaging test; (3) positive sorologic tests for human immunodeficiency virus (HIV), types A, B and C hepatitis, human T cell lymphotropic virus (HTLV), or Chagas disease; (4) significant heart valve disease (5) chronic renal disease in dialysis; (6) abusive use of alcohol and drugs; (7) any other medical condition with estimated survival<5 years; (8) participation in prior cell therapy studies; and (9) pregnancy.

A Phase I/IIa prospective Clinical Trial was conducted for a one-time surgical procedure wherein bone marrow mononuclear cells (prepared in accordance with Example 1) were injected intramyocardially at multiple injection points in patients suffering from refractory angina, with normal or slightly depressed left ventricular function. The patients' refractory angina was rigorously defined as functional Canadian Cardiovascular Society Angina Classification (CCSAC) class IV, with fully optimized pharmacological treatment, and without any medical or possible interventional procedure (CABG and PTCA)—"no option" patients.

For each patient, a total of 100 cc of bone marrow was aspirated from the iliac crest, and stored in a saline solution with 80 U.I. heparin/mL concentration. Mononuclear cells were isolated by density gradient, and diluted to a final concentration of $10^7$ cells/mL, in accordance with ReACT and Good Manufacturing Practices (GMP). Cell viability, total mononuclear, leukocyte differential counting and CD34+ content, as well as aerobe and anaerobe microbiology tests were performed. Samples for future evaluation were stored.

One series of multiple cell formulation injections into the left ventricular myocardium were performed surgically, through a left lateral thoracotomy, as follows: 0.2 mL ($2\times10^6$ cells)/injection, 1 cm distance between injections, and 1 cm epimyocardial depth infusion. The number of injections (40 to 90) for each patient differed based on the extension of myocardium viable ischemic area determined on nuclear imaging tests, magnetic resonance imaging (MRI), scintigraphic imaging, and left ventricular chamber enlargement.

Follow Up

Patients' heart rhythm was monitored for 48 hours after surgery. Clinical evaluation of CCSAC was carried at months 3, 6, 12, and 18 after surgery. Echocardiogram was performed at baseline and months 1, 3, 6 and 12 and heart magnetic resonance imaging at baseline and months 6 and 12 to assess safety. Nuclear imaging test (Tecnecium stress-induced myocardium perfusion scintigraphy and MRI) was performed at baseline and 6 and 12 months after the procedure to evaluate the percentage of myocardium ischemic area. It's important to point out, regarding ischemic heart area objective analysis (stress scintigraphy), that all patients were considered to have 100% of viable myocardium ischemic area on those specific left ventricular walls identified by stress tecnecium scintigraphy, prior to cell formulation injection. These reversible ischemic heart areas were considered baseline comparison to 6 and 12 months scintigraphic analysis follow-up. Scintigraphic analysis was only performed at 6 and 12 month follow-up.

Statistical Analysis

The Friedman non-parametric test was used to assess changes in angina CCSAC class at 3, 6 and 12 months and in myocardium ischemic area at 6 and 12 months of follow up. For post-hoc comparisons, the Wilcoxon test with Bonferroni's correction was used. Correlation between outcomes (angina class and myocardium ischemic area after the procedure) and the injections number was assessed by Spearman test. To compare the left ventricular function on echocardiogram before and 12 months after the procedure, the Wilcoxon non-parametric test was used.

As detailed below, the improvement in the myocardial perfusion of a patient (or lack thereof) correlated to the dose of monocyte lineage cells. Patients receiving the highest numbers of monocyte lineage cells showed a reduction of the angina class from IV to 0 (CCSAC).

Table 1A below shows the results of complete seroconversion (titers≥1:4) in human subjects immunized with recombinant proteins only or the recombinant proteins combined with OMV.

TABLE 1A

Age, gender, CCSAC prior to treatment, CCSAC six months after treatment, number of monocytes injected intramyocardially, and myocardial perfusion improvement six months after treatment.

| Patient | Age | Gender | Prior CCSAC | CCSAC 6 months after treatment | Number of intra-myocardial Monocytes injected (cell × 10⁶) | Myocardial Perfusion Improvement in 6 months (%) |
|---|---|---|---|---|---|---|
| 1 | 70 | male | 4 | 0 | 18.36 | 100 |
| 2 | 58 | male | 4 | 2 | 11.20 | 85 |
| 3 | 72 | female | 4 | 2 | 13.92 | 90 |
| 4 | 75 | male | 4 | 0 | 14.47 | 100 |
| 5 | 59 | female | 4 | 2 | 9.52 | 40 |
| 6 | 53 | male | 4 | 4 | 7.99 | 0 |
| 7 | 53 | female | 4 | 0 | 11.20 | 100 |

Table 1B below shows the variation in Angina Classification and Myocardium Ischemic Area after the BMMC monocytes enriched formulation infusion.

relation is statistically significant ($p<0.05$), thus demonstrating the efficacy of the methods and compositions as disclosed herein.

Figure 2:
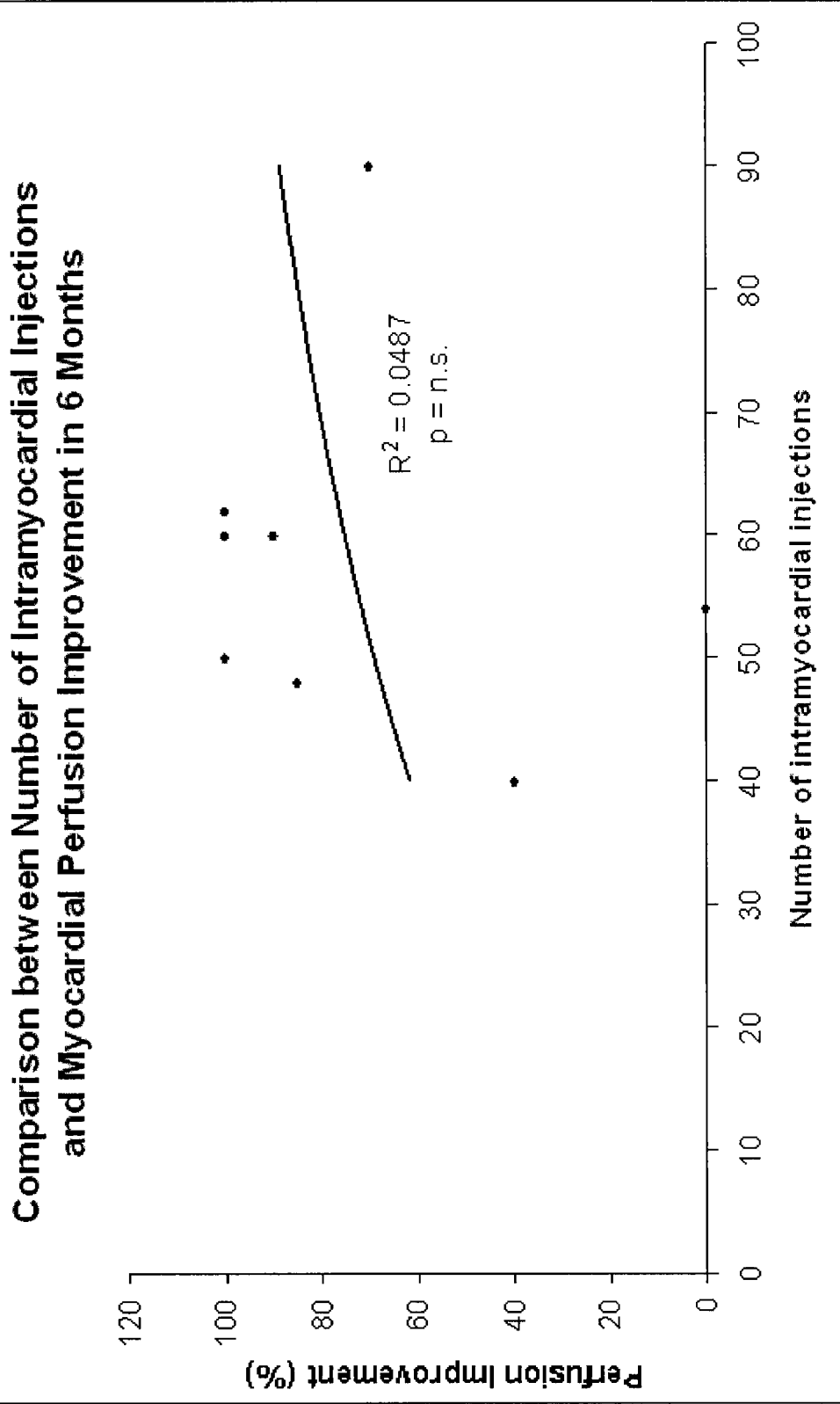
FIG. 2 shows a comparison between the number of intramyocardial injections (x-axis) and the myocardial perfusion improvement (%, y-axis) six months after cell therapy procedure. This graphic shows that the perfusion improvement is due to the cells injected and not to the physical impact of the needles or fluid infusion as there was no significant correlation was observed between the improvement in myocardial perfusion and the number injections ($p=n.s$; FD=6).

To rule out an effect due to number of injections (which to a degree also correlates to dose of monocyte lineage cells), the correlation between the number of injections and improvement in myocardial perfusion was determined FIG. 2 illustrates the lack of such correlation graphically. As indicated on FIG. 2, no statistically significant correlation was observed.

Subjective Improvement in Myocardial Ischemia

Figure 3:
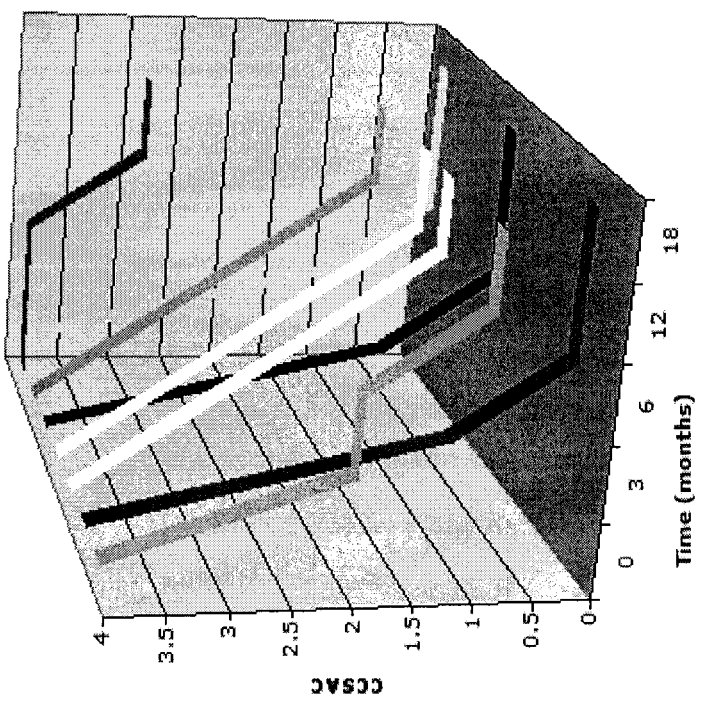
FIG. 3 shows variations in CCSAC in 18 month follow up. Each line in the graphic represents one patient enrolled in ReACT and the corresponding CCSAC improvement over 18 month follow-up. The x axis represents CCSAC class (number 4 for refractory angina pectoris, and number 0 for no pain). The y axis represents patient follow-up in months. The table on the left represents one-tailed Wilcoxon test statistical analysis of CCSAC improvement in 3, 6, 12 and 18 months follow-up. Related to baseline; variation in angina class is statistically significant if $p<0.0125$ (0.05/4) (Bonferroni's correction).

After the ReACT myocardial injection procedure, there was a progressive improvement in the angina classification median, varying from class 4 at baseline to 2.5 ($p=0.008$), 2 ($p=0.008$), 1 ($p=0.004$) and 1 ($p=0.004$) at 3, 6, 12 and 18 months of follow up, respectively (FIG. 3 and Table 2).

Table 2 below shows Spearman's correlation coefficients (rs) between BMMC Monocytes content, Lymphocytes and CD34+ cells and improvement of Angina Classification and % myocardium ischemic area in the follow up. For technical reasons, we don't have cell counting and percentage for the first patient enrolled in the study, with analysis for only 7 patients.

Table 2 below shows Spearman's correlation coefficients (rs) between BMMC Monocytes content, Lymphocytes and CD34+ cells and improvement of Angina Classification and % myocardium ischemic area in the follow up. For technical reasons, we don't have cell counting and percentage for the first patient enrolled in the study, with analysis for only 7 patients.

| | | Follow-up | | | | | |
|---|---|---|---|---|---|---|---|
| | | CCSAC** | | | | % ischemic area[&] | |
| Patient | Pre | 3 months | 6 months | 12 months | 18 months | Pre*** | 6 months | 12 months |
| 1 | 4 | 2 | 2 | 1 | 1 | 100 | 0 | 0 |
| 2 | 4 | 1 | 0 | 0 | 0 | 100 | 0 | 0 |
| 3 | 4 | 3 | 2 | 1 | 1 | 100 | 0 | 0 |
| 4 | 4 | 3 | 2 | 1 | 1 | 100 | 100 | 0 |
| 5 | 4 | 1 | 0 | 0 | 0 | 100 | 100 | 40 |
| 6 | 4 | 3 | 2 | 1 | 1 | 100 | 100 | 0 |
| 7 | 4 | 4 | 4 | 3 | 3 | 100 | 85 | 85 |
| 8 | 4 | 1 | 0 | 0 | 0 | 100 | 100 | 0 |
| Mean | 4 | 2.3 | 1.5 | 0.9 | 0.9 | 100 | 60.6 | 15.6 |
| Median | 4 | 2.5 | 2.0 | 1.0 | 1.0 | 100 | 92.5 | 0.0 |
| p value (Friedman test) | | <0.001 | | | | | 0.002 | |
| p value (unilateral Wilcoxon* test) | — | 0.008 | 0.008 | 0.004 | 0.004 | — | 0.063 | 0.004 |

***All patients were considered to have 100% of viable myocardium ischemic area on those specific left ventricular walls identified by stress tecnecium scintigraphy, prior to cell formulation injection. The 6 and 12 month analysis reflects the myocardium ischemic area percentage reduction on these walls.
**According to Canadian Cardiovascular Society Angina Classification
[&]Assessed by Stress Tecnecium Scintigraphy
*Related to baseline; variation in angina class and ischemic myocardium area statistically significant if $p < 0.0125$ (0.05/4) and $p < 0.025$ (0.05/2) (Bonferroni's correction); respectively mnths: months of follow up As can be seen from the data in table 1, there is a strong correlation between the number of monocytes injected intramyocardially and the reduction or elimination of angina symptoms and between the number of monocytes injected intramyocardially and the improvement in myocardial perfusion. FIG. 1 illustrates the second correlation graphically (i.e., the improvement of myocardial perfusion). Further, the cor-

| Angina Class* and % ischemia | | Monocytes | Lymphocytes | CD34+ |
|---|---|---|---|---|
| Angina Class*- 3 months | $r_s$ | −0.759 | 0.579 | −0.318 |
| | P value | 0.048 | 0.174 | 0.487 |
| | n | 7 | 7 | 7 |
| Angina Class*- 6 months | $r_s$ | −0.759 | 0.579 | −0.458 |
| | p value | 0.048 | 0.174 | 0.301 |
| | n | 7 | 7 | 7 |

| Angina Class* and % ischemia | | Monocytes | Lymphocytes | CD34+ |
|---|---|---|---|---|
| Angina Class*- | $r_s$ | −0.759 | 0.579 | −0.458 |
| 12 months | P value | 0.048 | 0.174 | 0.301 |
|  | n | 7 | 7 | 7 |
| Angina Class*- | r | −0.759 | 0.579 | −0.458 |
| 18 months | P value | 0.048 | 0.174 | 0.301 |
|  | n | 7 | 7 | 7 |
| % ischemic area<sup>&</sup> | $r_s$ | −0.101 | 0.339 | 0.077 |
| 6 months | P value | 0.830 | 0.457 | 0.869 |
|  | n | 7 | 7 | 7 |
| % ischemic area<sup>&</sup> | $r_s$ | −0.270 | 0.267 | −0.204 |
| 12 months | P value | 0.559 | 0.562 | 0.661 |
|  | n | 7 | 7 | 7 |

Figure 4:
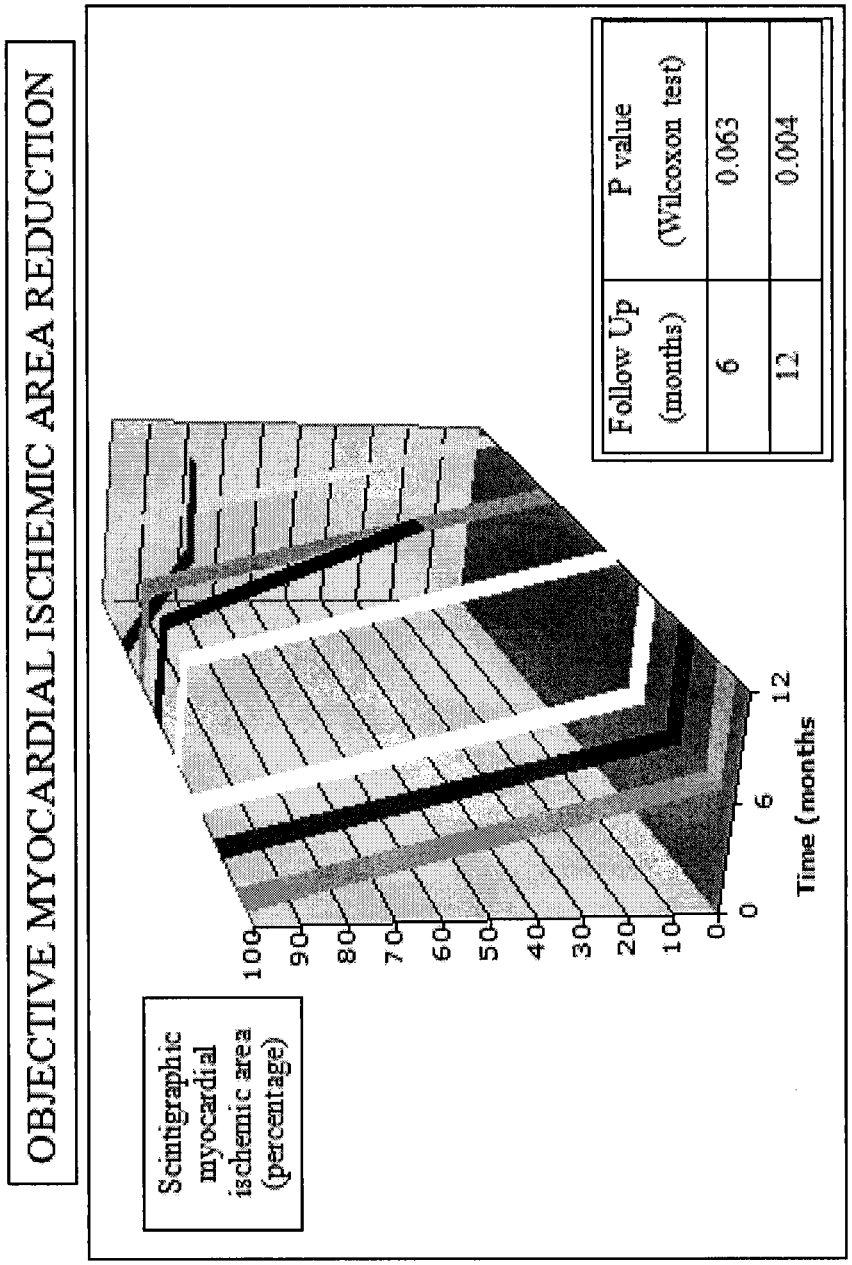
FIG. 4 shows variations in myocardial ischemic area evaluated by stress tecnecium scintigraphy in 12 month follow up. Each line in the graphic represents one patient enrolled in ReACT and the corresponding scintigraphic myocardium ischemic area improvement over 12 month follow-up. The x axis represents the percentage of scitigraphic myocardial ischemic area. The y axis represents patient follow-up in months (scintigraphic analysis was assessed only in 6 and 12 months). The table on the bottom right represents one-tailed Wilcoxon test statistical analysis of scintigraphic myocardium ischemic area improvement in 6 and 12 months follow-up. Related to baseline; variation in scintigraphic myocardium ischemic area improvement is statistically significant if $p<0.025$ (0.05/2) (Bonferroni's correction).
Figure 5:
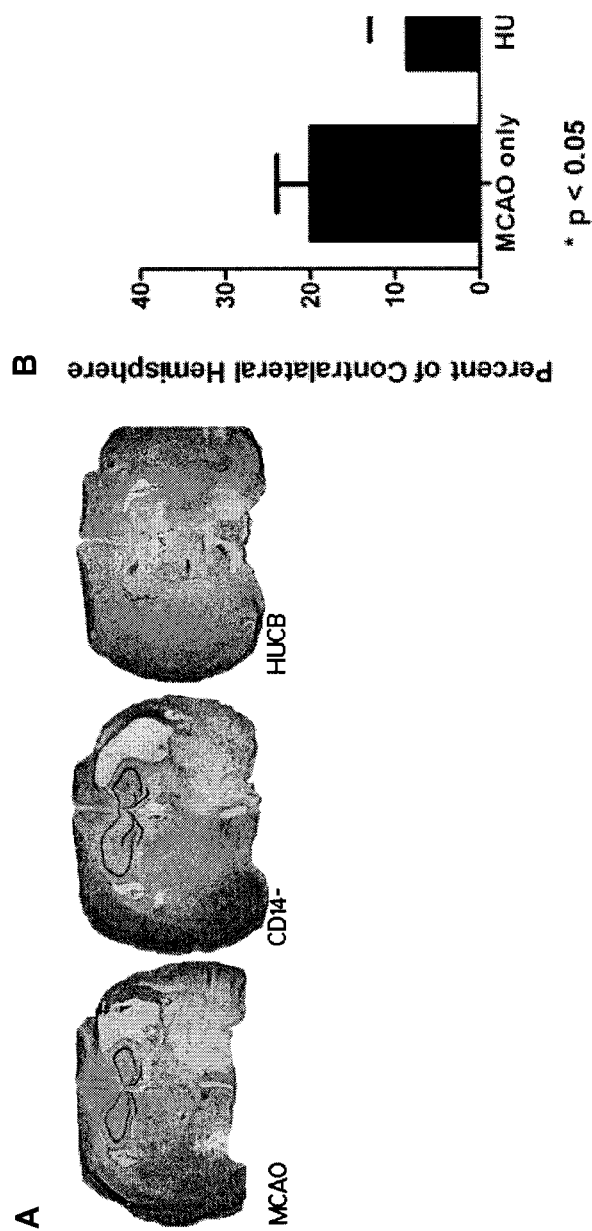
FIG. 5: Monocytes and macrophage are a critical component of cord blood for the repair of brain damage after middle cerebral artery occlusion (MCAO) in the rat. A) After MCAO, there is substantial damage in the ipsilateral hemisphere, particularly in striatum, hippocampus and cortex. HUCB treatment 48 hours after the MCAO reduces the lesion size while removal of the CD14+ monocytes and macrophage from the human umbilical cord blood (HUCB) fraction eliminates this effect. B) With the removal of CD14+ monocytes and macrophage from the HUCB, infarct volume after MCAO increased back to the level of infarct volume in untreated MCAO only rats. Infarct volume in the CD14 depleted group was significantly greater than in the HUCB treated group.
Figure 7:
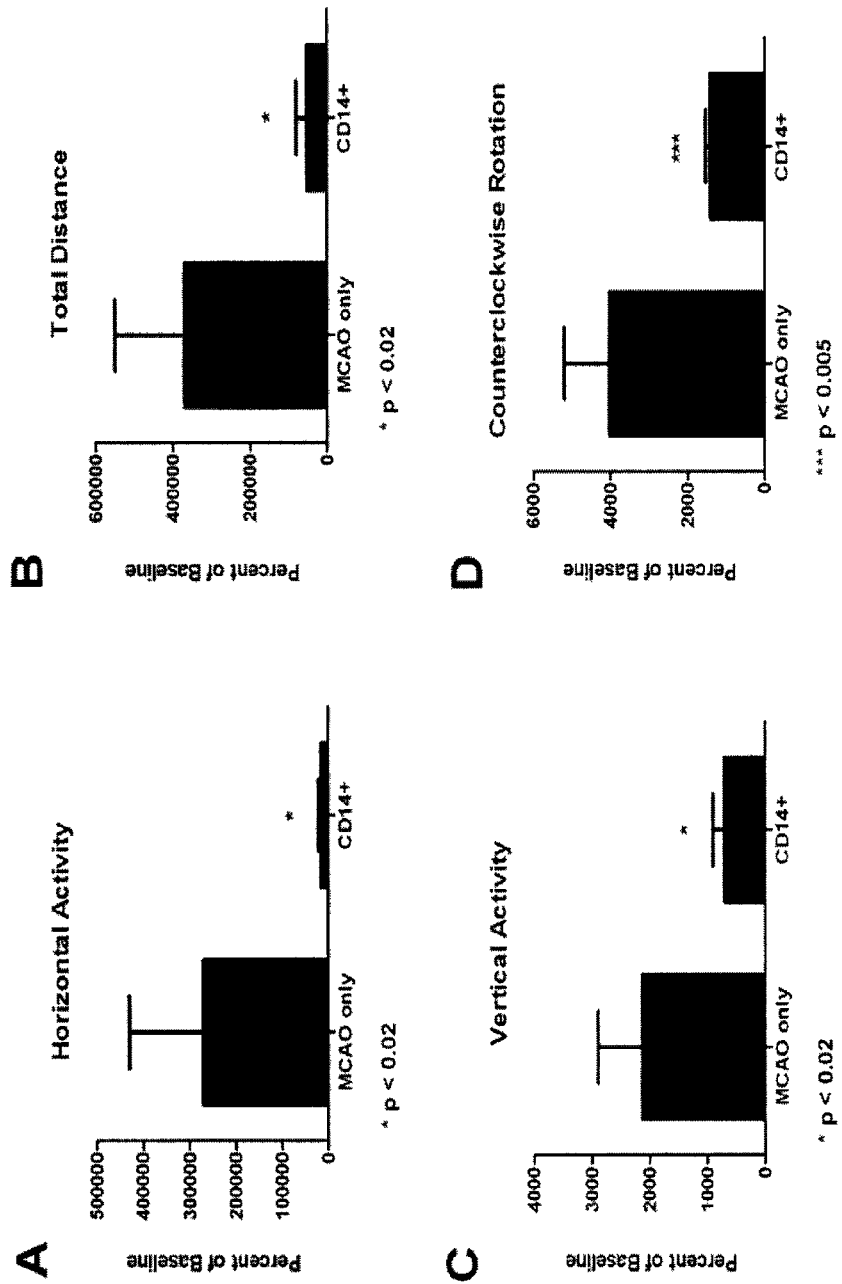
FIG. 7: Spontaneous Activity is reduced by CD14+ HUCB cell administration. After the MCAO, the rats become hyperactive. Administration of cord blood monocytes and macrophage decreases activity toward normal (baseline) levels on multiple parameters of movement, including A) horizontal activity, B) total distance traveled in the cage, C) vertical activity (rearing) and D) counterclockwise rotation.
Figure 8:
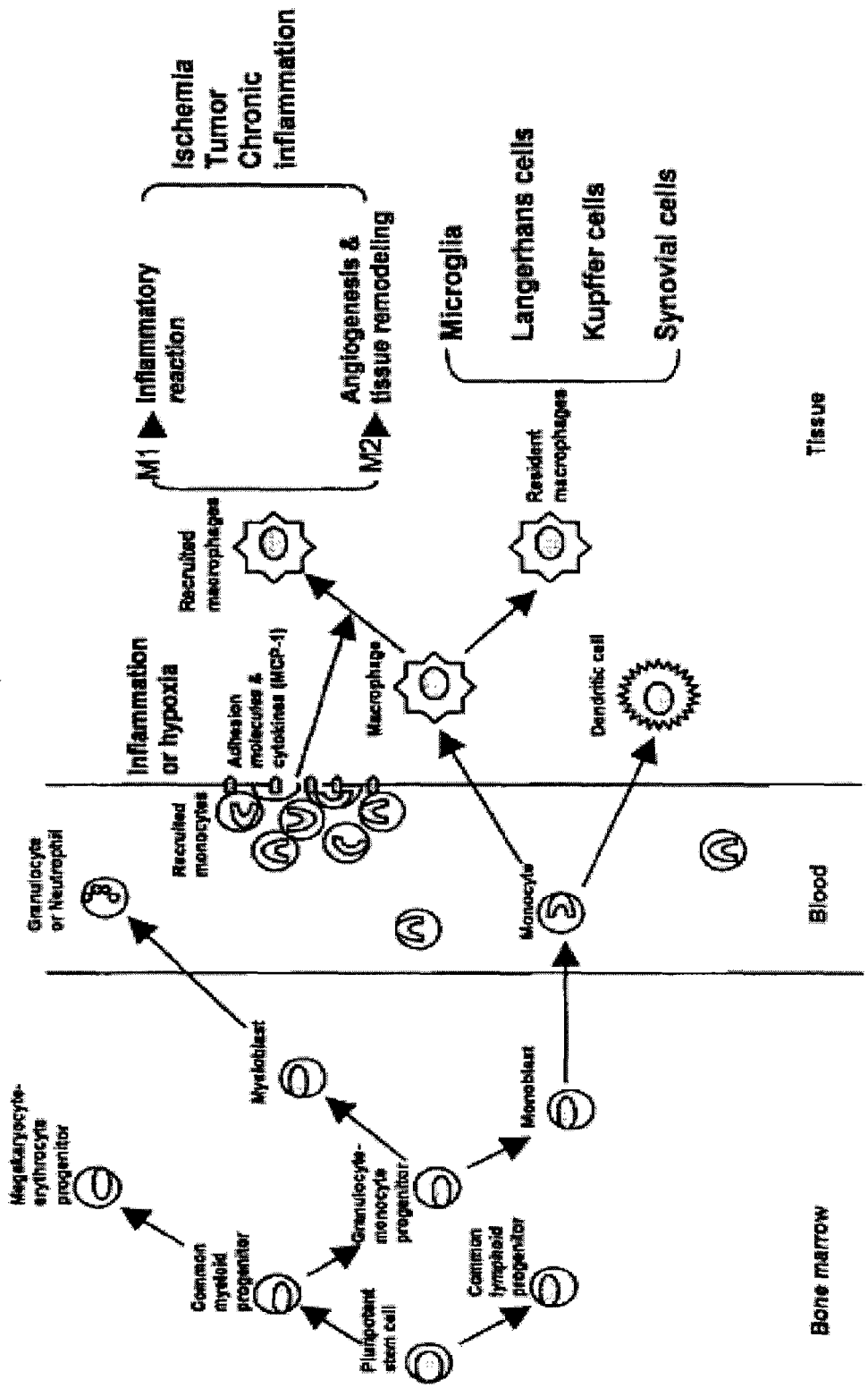
FIG. 8: Schematic diagram depicting monocyte/macrophage ontogeny. The pluripotent stem cells differentiate into myeloid or lymphoid progenitors in bone marrow. The granulocyte-monocyte progenitors are derived from the common myeloid progenitor cell before differentiating into myeloblast and monoblast. Monocytes are differentiated from monoblast and subsequently move from the bone marrow into the blood. Blood monocytes differentiate into various types of resident macrophages depending on their anatomical locations after extravasating into tissues. On the other hand, during the early inflammatory process, recruitment and transendothelial migration of circulating monocytes is augmented by a series of adhesion and chemotactic materials, expressed by inflammatory cells. Recruited monocytes migrate along chemotactic and oxygen gradients between normal and injured tissues, and accumulate within inflammatory and hypoxic cores in ischemia, or solid tumors, or chronic inflammatory diseases before differentiation into recruited macrophages which have polarization, M1 or M2 subset.

*According to Canadian Cardiovascular Society Angina Classification & Improvement assessed by stress technetium scintigraphy
months: months of follow up Objective Improvement in Myocardial Ischemia A progressive reduction in ischemic myocardium area was observed by stress tecnecium scintigraphy after 6 months (decrease of 39.4%, p=0.06) and 12 months (decrease of 84.4%, p<0.004), although the difference was statistically significant only at 12 months. It is important to note, that all patients were considered to have 100% of viable myocardium ischemic area on those specific left ventricular walls identified by stress tecnecium scintigraphy, prior to cell formulation injection. These initial reversible ischemic heart areas were considered baseline when compared to 6 and 12 months scintigraphic analysis follow-up. (FIG. 4 and Table 2).

Correlation Between ReACT's Formulation and Improvement

ReACT has a certain percentage of monocytes and its specific formulation positively correlates with clinical response; specifically, improvement in CCSAC (Table 3).

Other cell types such as Lymphocytes or CD34+ cells show no correlation with CCSAC or myocardium ischemic area improvement.

The results of this study demonstrate that ReACT may benefit refractory angina patients, who are not suitable for conventional myocardial revascularization, and show signs of angina at rest despite maximum medical therapy. Our findings demonstrate an improvement in angina symptoms and a decrease in the extent of myocardial ischemia. The probable causal mechanism of this improvement may be angiogenic properties of ReACT formulation.

In our study, angina symptom relief began as early as 3 months after the procedure and kept improving until the 12<sup>th</sup> month, with sustained improvement through the 18<sup>th</sup> month, suggesting that angiogenesis began early, and that it kept evolving 18 months after the procedure (see Table 2 and FIG. 3). Additionally, since symptom relief progressively improved in all patients, this suggests that is the effect is sustained and not transitory, a result different from other studies (6). Accordingly, the myocardial ischemia percentage showed a decreasing trend, ultimately reaching significance at 12 months. The fact that symptom improvement occurred much earlier than perfusion improvement might be explained by nuclear imaging test low spatial resolution and high variability, preventing it from detecting small changes, especially in such a small patient population.

The natural history of refractory angina shows that spontaneous remissions of even severe angina may occur (9, 31, 54, 60). Looking at the medically treated groups of randomized studies, between 0-19% of patients included in percutaneous myocardial laser revascularization trials and 0-32% for surgical myocardial laser revascularization studies had an improvement of at least two points in CCSAC over 12 months, and 0-44% at 3 years (38). Our results show a much compelling and greater CCSAC improvement, reinforced by the tangible myocardium perfusion stress testing.

Refractory angina studies included mainly patients with moderate to severe left ventricular dysfunction (13, 41, 57). As a result, our results showed better improvement in angina symptoms and quality of life, rather than benefits in left ventricular ejection fraction (LVEF). In our study, all patients had LVEF≥45% at baseline, and as expected, there was no significant change in LVEF at 12 months (p=0.726). These findings also suggest angiogenesis directly related to stem cell infusion and not myocardial punctures promoting secondary angiogenesis. On the other hand, the sustained LVEF as well the myocardial perfusion improvement suggests absence of functional deficit due to myocardium necrosis or fibrosis promoted by the intramyocardial ReACT injections, reinforcing the procedure safety.

The standard refractory angina patient population with viable myocardium and preserved left ventricular function would be the ideal candidate for an angiogenic therapy employing ReACT intramyocardial injection. For obvious reasons, analysis of LVEF is not an endpoint for this group. The primary therapeutic goal is myocardial perfusion improvements using ReACT formulation in a subjective (CCSAC) and objective (stress-induced myocardium imaging testing) perspective.

Different from other studies (12, 57), ReACT has an specific cell formulation, which seems to correlate with clinical and scintigraphic responses; an improvement in angina classification and a reduction in myocardium ischemic area, respectively. Improvement in CCSAC (subjective measure), followed by correlated reduction in myocardium ischemic area (objective measure) strongly suggests neoangiogenesis as the main stem cell action mechanism (FIGS. 3 and 4). Consequently, the large fraction of monocytes presented in the ReACT seems to be related to the angiogenesis that restores the perfusion on the myocardial ischemic areas after the cell transplantation. The mechanisms are not yet elucidated and will be analyzed in the next phase of this study. Nevertheless, a significant correlation between number of monocytes and improvement of clinical response (r=−0.759, p<0.05) strongly supports a cell related effect of ReACT in this study.

This positive correlation between the number of monocytes in ReACT and the sustained improvement in angina class could indicate the importance of these supporting cells for BMMC stem cells' mechanism of action and sustained myocardium angiogenesis. Also critical, these results support the hypothesis that the results of this study are due to a cellular effect of ReACT formulation and not to non-specific effects of the ReACT procedure. Future controlled studies will further clarify.

Bone marrow is a natural source of a broad spectrum of cytokines that are involved in the control of angiogenic and inflammatory processes. Bone marrow leukocytes play an important role in angiogenic mechanism, and neutrophils and monocytes act as a key in this process (10, 24, 29, 47).

The bone marrow monocytes or promonocytes can be activated in response to chemotactic stimuli and undergo final differentiation into macrophages. The macrophages play a key role in angiogenesis through their capacity to secrete proteases, growth factors, monokines, and influence each phase of the angiogenic process, including alterations of local extracellular matrix, induction of endothelial cells to migrate or proliferate, and inhibition of vascular growth with formation of differentiated capillaries (5, 10, 46, 51).

The optimal number or formulation of stem cells to promote myocardial regeneration remains controversial among different investigators, most of them showing no dose-dependent effect (18, 20). Iwasaki et al. (25) conducted one of the only studies that demonstrated a positive correlation between number of injected stem cells and myocardial regeneration in rats with experimental acute myocardial infarction. Henning et al. (23) injected human cord blood-derived bone marrow stem cells in infarcted rats, comparing different doses and routes of administration (intramyocardial, intracoronary or intravenous), demonstrating higher effectiveness with the intramyocardial injection. In our study, we performed ReACT, a single series of multiple injections with 2×106 BMMC formulation/myocardium puncture. There was no correlation between the number of injections and the angina classification variation over time, however the study population was probably too small for any significant association to be reached and as the ReACT Protocol is designed to continue, future data may or may not confirm this.

The intramyocardial route of cell formulation delivery was selected based upon experimental data that shows higher myocardial stem cell uptake through intramyocardial infusion, in comparison to other routes, such as intracoronary (either anterograde or retrograde injection) or transcoronary (33, 42, 50). Also, the chronic clinical feature of refractory angina provides a much safer profile for an intramyocardial approach, without major complication concerns, like intramyocardial injection in the acute setting (acute myocardial infarction). One study conducted by Perin et al. (42) analyzed the safety and feasibility of endomyocardial injection in acute myocardial infarction. There were no life threatening complications and the method seemed to be safe. Although, considerable arrhythmia risks cannot be ruled out if we consider direct intramyocardial injection in an acute unstable myocardium.

It is important to point out that, although promising, we understand our study has some limitations. While our study included a larger number of patients with a significantly greater follow-up time than most published refractory angina studies, the small sample size of 8 patients makes efficacy determination difficult, but has been able to demonstrate safety. Due to ethical aspects and the inability to justify the use of an isolated surgical intramyocardial placebo in this population, this was a non-randomized, open study; consequently, a placebo effect cannot be ruled out. However, it should be emphasized that objective increase in myocardium perfusion was also assessed and maintained over time.

Other clinical studies still need to confirm our results. However, the effectiveness of this ReACT procedure, in compliance with the technical and GMP specifications as well as a specific cell preparation of ReACT, seem to deliver better outcomes than previously reported by other investigators.

In conclusion, surgical intramyocardial transplantation of an autologous, bone marrow derived cell preparation, in a standardized protocol, may be a safe and effective procedure in promoting progressive and sustained improvement in patients with refractory angina.

REFERENCES

The following are references cited in example 2 and in the background section.
1. Abdel-Latif, A.; Bolli, R.; Tleyjeh, I. M.; Montori, V. M.; Perin, E. C.; Hornung, C. A.; Zuba-Surma, E. K.; Al-Mallah, M.; Dawn, B. Adult bone marrow-derived cells for cardiac repair. A systematic review and meta-analysis. Arch. Intern. Med. 167: 989-997; 2007.
2. Anversa, P; Leri, A; Rota, M; Hosoda, T; Bearzi, C; et al. Concise review: stem cells, myocardial regeneration, and methodological artifacts. Stem Cells 2007; 25: 589-601.
3. Beeres, S L M A; Bax, J J; Dibbets-Schneider, P; Stokkel, M P M; Fibbe, W E; et al. Sustained effect of autologous bone marrow mononuclear cell injection in patients with refractory angina pectoris and chronic myocardial ischemia: twelve-month follow-up results. Am Heart J 2006; 152: 684.e11-684.e16.
4. Beeres, S L M A; Bax, J J; Kaandorp, T A; Zeppenfeld, K; Lamb, H J; et al. Usefulness of intramyocardial injection of autologous bone marrow-derived mononuclear cells in patients with severe angina pectoris and stress-induced myocardial ischemia. Am. J. Cardiol. 2006; 97: 1326-31.
5. Benelli, R; Albini, A; Noonan, D. Neutrophils and angiogenesis: potential initiators of the angiogenic cascade. Cassatella M A (ed): The Neutrophil. Chem Immunol Allergy. Basel, Karger, 2003, vol 83, pp. 167-181.
6. Briguori, C; Reimers, B; Sarais, C; Napodano, M; Pascotto, P; et al. Direct intramyocardial percutaneous delivery of autologous bone marrow in patients with refractory myocardial angina. Am Heart J 2006; 151: 674-80.
7. Charwat, S.; Gyöngyösi, M; Lang, I; Graf, S; Beran, G; et al. Role of adult bone marrow stem cells in the repair of ischemic myocardium: current state of the art. Experimental Hematology 2008; 36: 672-80.
8. Cogle, C R; Madlambayan, G J; Hubsher, G; Beckman, C; Speisman, R; et al. Marrow cell therapies for cardiovascular diseases. Experimental Hematology 2008; 36: 687-94.
9. DeJongste, M J L; Tio, R A; Foreman, R D. Chronic therapeutically refractory angina pectoris. Heart 2004; 90: 225-30.
10. Dirkx, A E M; oude Egbrink, M G A; Wagstaff, J; Griffioen, A W. Monocyte/macrophage infiltration in tumors: modulators of angiogenesis. J Leukoc Biol 2006; 80: 1183-96.
11. Fraker, Jr, T D; et al. 2007 Chronic Angina Focused Update of the ACC/AHA 2002 Guidelines for the Management of Patients With Chronic Stable Angina: A Report of the American College of Cardiology/American Heart Association Task Force on Practice Guidelines Writing Group to Develop the Focused Update of the 2002 Guidelines for the Management of Patients With Chronic Stable Angina. Circulation, 2007; 116: 2762-72.
12. Fuchs, S; Kornowski, R.; Weisz, G; Satler, L F; Smits, P C; et al. Safety and feasibility of transendocardial autologous bone marrow cell transplantation in patients with advanced heart disease. Am J Cardiol 2006; 97: 823-9.
13. Fuchs, S; Satler, L F; Kornowski, R.; Okubagzi, P; Weisz, G; et al. Catheter-based autologous bone marrow myocardial injection in no-option patients with advanced coronary artery disease. A feasibility study. J. Am. Coll. Cardiol. 2003; 41: 1721-4.
14. Gibbons, R J; et al. ACC/AHA 2002 Guideline Update for the Management of Patients With Chronic Stable Angina—Summary Article. A Report of the American College of Cardiology/American Heart Association Task Force on Practice Guidelines (Committee on the Management of Patients With Chronic Stable Angina). Circulation 2003; 107: 149-58.
15. Gordon, M Y. Stem cells for regenerative medicine—Biological attributes and clinical application. Experimental Hematology 2008; 36: 726-32.
16. Guan, K; Hasenfuss, G. Do stem cells in the heart truly differentiate into cardiomyocites? J Molecular and Cellular Cardiology 2007; 43: 377-83.

17. Haider, H K h; Ashraf, M. Bone marrow stem cell transplantation for cardiac repair. Am J Physiol Heart Circ Physiol 2005; 288: 2557-67.
18. Hale, S L; Dai, W; Dow, J S; Kloner, R A. Mesenchymal stem cell administration at coronary artery reperfusion in the rat by two delivery routes: a quantitative assessment. Life Sciences 2008; 83: 511-5.
19. Hamano, K; Nishida, M; Hirata, K; Mikamo, A; Li, T-S; et al. Local implantation of autologous bone marrow cells for therapeutic angiogenesis in patients with ischemic heart disease—Clinical trial and preliminary results. Jpn Circ J 2001; 65: 845-7.
20. Hashemi, S M; Ghods, S; Kolodgie, F D; Parcham-Azad, K; Keane, M; et al. A placebo controlled, dose-ranging, safety study of allogenic mesenchymal stem cells injected by endomyocardial delivery after an acute myocardial infarction. European Heart J 2008; 29: 251-9.
21. Hattori, R; Matsubara, H. Therapeutic angiogenesis for severe ischemic heart diseases by autologous bone marrow cells transplantation. Molecular Cellular Biochemistry 2004; 264: 151-5.
22. Henning, R J; Abu-Ali, H; Balis, J U; Morgan, M B; Willing, A E; et al. Human Umbilical cord blood mononuclear cells for the treatment of acute myocardial infarction. Cell Transplantation 2004; 13: 729-39.
23. Henning, R J; Burgos, J D; Vasko, M; Alvarado, F; Sanberg, C D, et al. Human cord blood cells and myocardial infarction: effect of dose and route of administration on infarct size. Cell Transpl 2007; 16 (9): 907-17.
24. Hoefer, I E; Grundmann, S; van Royen, N; Voskuil, M; Schirmer, S H; et al. Leukocyte subpopulations and arteriogenesis: specific role of monocytes, lymphocytes and granulocytes. Atherosclerosis 2005; 181: 285-93.
25. Iwasaki, H; Kawamoto, A; Ishikawa, M; Oyamada, A; Nakamori, S; et al. Dose-dependent contribution of CD34-positive cell transplantation to concurrent vasculogenesis and cardiomyogenesis for functional regenerative recovery after myocardial infarction. Circulation 2006; 113: 1311-25.
26. Jolicoeur, E M; Granger, C B; Henry, T D; Holmes, D J; Pepine, C J; et al. Clinical and research issues regarding chronic advanced coronary artery disease: Part I: Contemporary and emerging therapies. Am Heart J 2008; 155: 418-34.
27. Kang, S; Yang, Y-j; Li, C-j; Gao, R-l. Effects of intracoronary autologous bone marrow cells on left ventricular function in acute myocardial infarction: a systematic review and meta-analysis for randomized controlled trials. Coronary artery disease 2008; 19: 327-35.
28. Kinnaird T; Stabile E; Burnett M S; Epstein S E. Bone marrow-derived cells for enhancing collateral development: mechanisms, animal data, and initial clinical experiences. Circ Res 2004; 95: 354-63.
29. Kusumanto, Y H; Dam, W A; Hospers, G A P; Meijer, C; Mulder, N H. Platelets and granulocytes, in particular the neutrophils, form important compartments for circulating vascular endothelial growth factor. Angiogenesis 2003; 6: 283-7.
30. Laflamme, M A; Zbinden, S; Epstein, S E; Murry, C E. Cell-based therapy for myocardial ischemia and infarction: pathophysiological mechanisms. Ann Rev Pathol Mech Dis 2007; 2: 307-39.
31. Leon, M B; Kornowski, R; Downey, W E; Weisz, G; Baim, D S; et al. A blinded, randomized, placebo-controlled trial of percutaneous laser myocardial revascularization to improve angina symptoms in patients with severe coronary disease. J Am Coll Cardiol. 2005; 46: 1812-9.
32. Lipinski, M J; Biondi-Zoccai, G G L; Abbate, A; Khianey, R; Sheiban, I; et al Impact of intracoronary cell therapy on left ventricular function in the setting of acute myocardial infarction: A collaborative systematic review and meta-analysis of controlled clinical trials. J Am Coll Cardiol 2007; 50: 1761-7.
33. Losordo, D W; Renault, M-A. Therapeutic myocardial angiogenesis. Microvascular Research 2007; 74: 159-71.
34. Losordo, D W; Schatz, R A; White, C J; Udelson, J E; Veereshwarayya, V; et al. Intramyocardial transplantation of autologous CD34+ stem cells for intractable angina: A phase I/IIa double-blind, randomized controlled trial. Circulation 2007; 115: 3165-72.
35. Mannheimer, C; Camici, P; Chester, M R; Collins, A; DeJongste, M; et al. The problem of chronic refractory angina. Report from de ESC joint study group on the treatment of refractory angina. Eur Heart J 2002; 23: 355-70.
36. Moore, R K; Groves, D.; Bateson, S.; Barlow, P; Hammond, C; et al. Health related quality of life of patients with refractory angina before and one year after enrolment onto a refractory angina program. European Journal of Pain 2005; 9: 305-10.
37. Mukherjee, D; Bhatt, D; Roe, M T; Patel, V; Ellis, S G. Direct myocardial revascularization and angiogenesis: how many patients might be eligible? Am J Cardiol 1999; 84: 598-600.
38. Nordrehaug, J E; Salem, M. Treatment of chronic refractory angina pectoris—light at the end of the tunnel? European Heart J 2006; 27: 1007-9.
39. Norol F; Merlet P; Isnard R; et al. Influence of mobilized stem cells on myocardial infarct repair in a nonhuman primate model. Blood 2003; 102: 4361-68.
40. Orlic D; Kajstura J; Chimenti S; et al. Bone marrow cells regenerate infarcted myocardium. Nature 2001; 410: 701-5.
41. Perin, E C; Dohmann, H F R; Borojevic, R; Silva, S A; Sousa, A L S; et al. Transendocardial, autologous bone marrow cell transplantation for severe, chronic ischemic heart failure. Circulation 2003; 107: 2294-2302.
42. Perin, E C; Silva, G V; Assad, J A R; Vela, D; Buja, L M; et al. Comparison of intracoronary and transendocardial delivery of allogeneic mesenchymal cells in a canine model of acute myocardial infarction. J Molecular Cellular Cardiology 2008; 44: 486-95.
43. Rana, J S; Mannam, A; Donnell-Fink, L; Gervino, E V; Sellke, F W; et al. Longevity of the placebo effect in the therapeutic angiogenesis and laser myocardial revascularization trials in patients with coronary heart disease. Am J Cardiol 2005; 95: 1456-9.
44. Rosenzweig, A. Cardiac cell therapy—Mixed results from mixed cells. N Eng J Med 2006; 355 (12): 1274-7.
45. Saririan, M; Eisenberg, M J. Myocardial laser revascularization for the treatment of end-stage coronary artery disease. J Am Coll Cardiol 2003; 41: 173-83.
46. Scapini, P; Morini, M; Tecchio, C; Minghelli, S; Di Carlo, E; et al. CXCL1/Macrophage inflammatory protein-2-induced angiogenesis in vivo is mediated by neutrophil-derived vascular endothelial growth factor-A. The Journal of Immunology 2004; 172: 5034-40.
47. Schruefer, R; Lutze, N; Schymeinsky, J; Walzog, B. Human neutrophils promote angiogenesis by a paracrine feedforward mechanism involving endothelial interleukin-8. Am J Physiol Heart Circ Physiol 2005; 288: H1186-H1192.
48. Schuldt, A J T; Rosen, M R; Gaudette, G R; Cohen, I S. Repairing damaged myocardium: evaluating cells used for cardiac regeneration. Current Treatment Options Cardiovascular Medicine 2008; 10: 59-72.
49. Steinhoff, G; Choi, Y-H; Stamm, C. Intramyocardial bone marrow stem cell treatment for myocardial regeneration. European Heart J Supplements 2006; 8(Sup. H): H32-H39.
50. Sun, Z; Wu, J; Fujii, H; Wu, J; Li, S-H; Porozov S, Belleli A, Fulga V, Porat Y, Li R K. Human angiogenic cell precursors restore function in the infarcted heart: a comparison of cell delivery routes. European J Heart Failure 2008; 10: 523-33.
51. Sunderkötter, C; Steinbrink, K; Goebeler, M; Bhardwaj, R; Sorg, C. Macrophages and angiogenesis. J Leukoc Biol 1994; 55: 410-22.
52. Ting, A E; Mays, R W; Frey, M R; H of, W V; Medicetty, S; et al. Therapeutic pathways of adult stem cell repair. Critical Reviews Oncology/Hematology 2008; 65: 81-93.
53. Tse, H-F; Kwong, Y-L; Chan, J K F; Lo, G; Ho, C-L; et al. Angiogenesis in ischaemic myocardium by intramyocardial autologous bone marrow mononuclear cells implantation. Lancet, 2003; 361: 47-49.
54. Tse, H-F; Siu, C-W; Zhu, S-G; Songyan, L; Zhang, Q-Y; et al. Paracrine effects of direct intramyocardial implantation of bone marrow derived cells to enhance neovascularization in chronic ischaemic myocardium. European J Heart Failure 2007; 9: 747-53.
55. Tse, H-F; Thambar, S.; Kwong, Y-L; Rowlings, P; Bellamy, G; McCrohon J, Bastian B, Chan J K, Lo G, Ho C L, Lau C P. Safety of catheter-based intramyocardial autologous bone marrow cells implantation for therapeutic angiogenesis. Am J Cardiol 2006; 98: 60-2.
56. Tse, H-F; Thambar, S.; Kwong, Y-L; Rowlings, P; Bellamy, G; McCrohon J, Bastian B, Chan J K, Lo G, Ho C L, Parker A, Hauser T H, Lau C P. Comparative evaluation of long-term clinical efficacy with catheter-based percutaneous intramyocardial autologous bone marrow cell implantation versus laser myocardial revascularization in patients with severe coronary artery disease. Am Heart J 2007; 154: 982.e1-982.e6.
57. Tuma-Mubarak, J; Fernández-Viña, R; Carrasco-Yalán, A; Castillo-Aguirre, J; Ríos-Díaz, H; et al. Refractory angina treatment by percutaneous retrograde sinus technique transplantation of unselected autologous bone marrow mononuclear cells: long-term follow-up. Abstracts, Cardiovasc Revascularization Med 2007; 8: 153-4.
58. van Ramshorst, J.; Bax, J. J.; Beeres, S. L.; Dibbets-Schneider, P.; Roes, S. D.; Stokkel, M. P.; de Roos, A.; Fibbe, W. E.; Zwaging a, J. J.; Boersma, E.; Schalij, M. J.; Atsma, D. E. Intramyocardial bone marrow cell injection for chronic myocardial ischemia: a randomized controlled trial. JAMA 301(19):1997-2004; 2009.
59. Vicario, J; Campo, C; Piva, J; Faccio, F; Gerardo, L; et al. One-year follow-up of transcoronary sinus administration of autologous bone marrow in patients with chronic refractory angina. Cardiovasc. Revascularization Med. 2005; 6: 99-107.
60. Yang, E H; Barsness, G W; Gersh, B J; Chandrasekaran, K; Lerman, A. Current and future treatment strategies for refractory angina. Mayo Clin. Proc. 2004; 79 (10): 1284-92.

Example 3

Monocytes for Brain Ischemia

Molecular Biology Techniques

Standard molecular biology techniques known in the art and not specifically described are generally followed as in Sambrook et al., Molecular Cloning: A Laboratory Manual, Cold Springs Harbor Laboratory, New York (1989, 1992), and in Ausubel et al., Current Protocols in Molecular Biology, John Wiley and Sons, Baltimore, Md. (1989). Polymerase chain reaction (PCR) is carried out generally as in PCR Protocols: A Guide to Methods and Applications, Academic Press, San Diego, Calif. (1990). Reactions and manipulations involving other nucleic acid techniques, unless stated otherwise, are performed as generally described in Sambrook et al., Molecular Cloning: A Laboratory Manual, Cold Springs Harbor Laboratory Press, and methodology as set forth in U.S. Pat. Nos. 4,666,828; 4,683,202; 4,801,531; 5,192,659; and 5,272,057 and incorporated herein by reference. In situ PCR in combination with Flow Cytometry can be used for detection of cells containing specific DNA and mRNA sequences (see, for example, Testoni et al., Blood, 1996, 87:3822).

Standard methods in immunology known in the art and not specifically described are generally followed as in Stites et al. (Eds.), Basic And Clinical Immunology, $8^{th}$ Ed., Appleton & Lange, Norwalk, Conn. (1994); and Mishell and Shigi (Eds.), Selected Methods in Cellular Immunology, W.H. Freeman and Co., New York (1980).

Immunoassays

In general, immunoassays are employed to assess a specimen such as for cell surface markers or the like. Immunocytochemical assays are well known to those skilled in the art. Both polyclonal and monoclonal antibodies can be used in the assays. Where appropriate other immunoassays, such as enzyme-linked immunosorbent assays (ELISAs) and radioimmunoassays (RIA), can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771; and 5,281,521 as well as Sambrook et al., Molecular Cloning: A Laboratory Manual, Cold Springs Harbor, N.Y., 1989. Numerous other references also may be relied on for these teachings.

Antibody Production

Antibodies may be monoclonal, polyclonal, or recombinant. Conveniently, the antibodies may be prepared against the immunogen or immunogenic portion thereof, for example, a synthetic peptide based on the sequence, or prepared recombinantly by cloning techniques or the natural gene product and/or portions thereof may be isolated and used as the immunogen Immunogens can be used to produce antibodies by standard antibody production technology well known to those skilled in the art as described generally in Harlow and Lane, Antibodies: A Laboratory Manual, Cold Spring Harbor Laboratory, Cold Springs Harbor, N.Y. (1988) and Borrebaeck, Antibody Engineering—A Practical Guide by W.H. Freeman and Co. (1992). Antibody fragments may also be prepared from the antibodies and include Fab and F(ab')2 by methods known to those skilled in the art. For producing polyclonal antibodies a host, such as a rabbit or goat, is immunized with the immunogen or immunogenic fragment, generally with an adjuvant and, if necessary, coupled to a carrier; antibodies to the immunogen are collected from the serum. Further, the polyclonal antibody can be absorbed such that it is monospecific. That is, the serum can be exposed to related immunogens so that cross-reactive antibodies are removed from the serum rendering it monospecific.

For producing monoclonal antibodies, an appropriate donor is hyperimmunized with the immunogen, generally a mouse, and splenic antibody-producing cells are isolated. These cells are fused to immortal cells, such as myeloma cells, to provide a fused cell hybrid that is immortal and secretes the required antibody. The cells are then cultured, and the monoclonal antibodies harvested from the culture media.

For producing recombinant antibodies, messenger RNA from antibody-producing B-lymphocytes of animals or hybridoma is reverse-transcribed to obtain complementary DNAs (cDNAs). Antibody cDNA, which can be full or partial length, is amplified and cloned into a phage or a plasmid. The cDNA can be a partial length of heavy and light chain cDNA, separated or connected by a linker The antibody, or antibody fragment, is expressed using a suitable expression system. Antibody cDNA can also be obtained by screening pertinent expression libraries. The antibody can be bound to a solid support substrate or conjugated with a detectable moiety or be both bound and conjugated as is well known in the art. (For a general discussion of conjugation of fluorescent or enzymatic moieties see Johnstone & Thorpe, Immunochemistry in Practice, Blackwell Scientific Publications, Oxford, 1982). The binding of antibodies to a solid support substrate is also well known in the art. (see for a general discussion Harlow & Lane, Antibodies: A Laboratory Manual, Cold Spring Harbor Laboratory Publications, New York, 1988 and Borrebaeck, Antibody Engineering—A Practical Guide, W.H. Freeman and Co., 1992). The detectable moieties contemplated with the present invention can include, but are not limited to, fluorescent, metallic, enzymatic and radioactive markers. Examples include biotin, gold, ferritin, alkaline phosphates, galactosidase, peroxidase, urease, fluorescein, rhodamine, tritium, $^{14}C$, iodination and green fluorescent protein.

Gene Therapy

Gene therapy as used herein refers to the transfer of genetic material (e.g., DNA or RNA) of interest into a host to treat or prevent a genetic or acquired disease or condition. The genetic material of interest encodes a product (e.g., a protein, polypeptide, and peptide, functional RNA, antisense) whose in vivo production is desired. For example, the genetic material of interest encodes a hormone, receptor, enzyme polypeptide or peptide of therapeutic value. Alternatively, the genetic material of interest encodes a suicide gene. For a review see "Gene Therapy" in Advances in Pharmacology, Academic Press, San Diego, Calif., 1997.

Administration of Cells for Transplantation

The monocytes of the present invention can be administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art.

In the method of the present invention, the monocytes of the present invention can be administered in various ways as would be appropriate to implant in the central nervous system, including but not limited to parenteral, including intravenous and intraarterial administration, intrathecal administration, intraventricular administration, intraparenchymal, intracranial, intracisternal, intrastriatal, and intranigral administration. Optionally, the umbilical cord blood cells are administered in conjunction with an immunosuppressive agent.

Pharmaceutical compositions comprising effective amounts of umbilical cord blood cells are also contemplated by the present invention. These compositions comprise an effective number of cells, optionally, in combination with a pharmaceutically acceptable carrier, additive or excipient. In certain aspects of the present invention, cells are administered to the patient in need of a transplant in sterile saline. In other aspects of the present invention, the cells are administered in Hanks Balanced Salt Solution (HBSS) or Isolyte S, pH 7.4. Other approaches may also be used, including the use of serum free cellular media. Systemic administration of the cells to the patient may be preferred in certain indications, whereas direct administration at the site of or in proximity to the diseased and/or damaged tissue may be preferred in other indications.

Pharmaceutical compositions according to the present invention preferably comprise an effective number within the range of about $1.0 \times 10^4$ cells to about $1.0 \times 10^9$ cells, more preferably about $1 \times 10^5$ to about $1 \times 10^7$ cells, even more preferably about $2 \times 10^5$ to about $8 \times 10^6$ cells generally in solution, optionally in combination with a pharmaceutically acceptable carrier, additive or excipient.

Preferably the monocytes are administered with a blood brain barrier permeabilizer. In one embodiment, the cells are combined with the permeabilizer prior to administration into the patient. In another embodiment, the cells are administered separately to the patient from the permeabilizer. Optionally, if the cells are administered separately from the permeabilizer, there is a temporal separation in the administration of the cells and the permeabilizer. The temporal separation may range from about less than a minute in time, to about hours or days in time. The determination of the optimal timing and order of administration is readily and routinely determined by one of ordinary skill in the art.

Throughout this application, various publications are referenced. The disclosures of all of these publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

One interesting function of monocytes/macrophages is to promote angiogenesis related to inflammatory reactions. Angiogenesis (or neovascularization) is a major element of inflammatory processes including subsequent repair cascades [Sunderkotter, 1994 #4]. During the early inflammatory process, circulating blood monocytes extravasate into tissues [Bosco, 2008 #3]. Initially, neighboring endothelial and inflammatory cells regulate this monocyte passing through vessel wall by releasing of a series of adhesion and chemotactic materials [Baggiolini, 2000 #9; Imhof, 2004 #2; Bosco, 2008 #3]. Along chemotactic and oxygen gradients between normal and injured tissues, extravasated monocytes move and gather into hypoxic and/or necrotic cores of diseased tissues before differentiation into tissue macrophages. The representative pathologic tissues to which monocytes/macrophages are apt to accumulate are as follows: solid tumors, myocardial or cerebral infarction, synovial joints of chronic arthritis or atheromatous plaques, bacterial infection, and healing wounds [Baggiolini, 2000 #9; Murdoch, 2004 #1; Bosco, 2008 #3; Mantovani, 2002 #15] (FIG. 1).

After differentiation from monocytes, macrophages in tissue have been known to exist as polarized populations, M1 and M2 subsets [Mantovani, 2004 #67; Sica, 2006 #16; Mantovani, 2004 #67; Mantovani, 2002 #15]. While M1 polarized macrophages are powerful inflammatory cells that produce pro-inflammatory cytokines and phagocytize pathogens, M2 macrophages modulate the inflammatory responses and help on angiogenesis and tissue repair [Mantovani, 2004 #67; Sica, 2006 #16; Mantovani, 2004 #67; Mantovani, 2002 #15]. Interestingly, in gene expression of macrophages, a combination of M1 and M2 subsets early in wound healing turns into dominantly M2 genes later [Deonarine, 2007 #68]. During the early stage of the wound healing process, M1 macrophages lead to an direct inflammatory reaction that clean up the wound and debris of microbes and/or injured host tissues whereas tissue repair and angiogenesis are begun by M2 macrophages at the same time. In the late stage when the cleansing by M1 macrophages is almost over, the prevailing M2 macrophages go on with their work, tissue regeneration including angiogenesis [Deonarine, 2007 #68]. Accumulating evidence suggests that recruited monocytes/macrophages aid in modulating and regulating neovascularization in ischemic tissue, tumors, and chronic inflammation such as arthritic joints and atherosclerosis.

Angiogenesis in Ischemia

In recent years, the importance of circulating monocytes/macrophages in neovascularization has been demonstrated in ischemic diseases [Shireman, 2007 #23; Herold, 2004 #33; Capoccia, 2008 #32]. Arteriogenesis, the structural growth of pre-established arteriolar webs into true effective collateral arteries, seems to be initiated by fluid shear stress increase which results from arterial obstruction, within the developing collateral arteries and not induced by tissue hypoxia and ischemia [Ito, 1997 #41; Heil, 2006 #19]. In contrast, angiogenesis, the formation of new capillaries from pre-existing blood vessels, is induced by hypoxia, and capillary density gets dense in sites of severe and acute ischemia [Scholz, 2002 #20; Ito, 1997 #41].

While arteriogenesis and angiogenesis, both induce neovascularization through different mechanisms, monocytes/macrophages essentially contribute to both actions. In arteriogenesis, abrupt arterial flow obstruction resulting from an embolus or a progressive stenosis increases fluid shear stress in the arteriolar web, and subsequently adhesion molecules and chemokines such as endothelial adhesion molecules [Nagel, 1994 #21] and monocyte chemotactic protein-1 (MCP-1) [Eischen, 1991 #22] increase significantly. Blood monocytes are activated and are drawn to the collateral artery by MCP-1. Once there, they go through the vessel wall by way of binding to adhesion molecules and/or differentiate into tissue macrophages before producing plenty of growth factors and cytokines [Sunderkotter, 1994 #4], which can promote endothelial and smooth muscle cell proliferation [Heil, 2006 #19; Shireman, 2007 #23].

Angiogenesis is a combination of more intricate processes, many of which are regulated by vascular endothelial growth factor (VEGF) and its receptors (VEGFR) which are known to initiate angiogenesis [Shireman, 2007 #23]. Recent data suggests, some subsets of angiopoietins (Ang-1 and 2) and their receptors (Tie) are critical to the secondary stages of the angiogenic process such as maturation, stabilization, and remodeling of vessels [Thurston, 2003 #57]. Hypoxia and tissue necrosis affect significantly production of VEGF/VEGFR and angiopoietin/Tie receptors [Milkiewicz, 2006 #24; Zhang, 2005 #56; Beck, 2000 #58; Murdoch, 2007 #59].

In turn, VEGF and angiopoietin induce the recruitment of endothelial progenitor cells and monocytes/macrophages [Tammela, 2005 #25; Murdoch, 2007 #59].

Recruited monocytes/macrophages promote angiogenesis by several potential mechanisms as follows. First, macrophages degrade the extracellular matrix using matrix metalloproteinases and proteolytic enzymes, leading to endothelial cell migration [Moldovan, 2005 #26]. Via a path through the extracellular matrix, growth factors and endothelial cells are mobilized from established vessels to form new capillaries [Shireman, 2007 #23].

Second, monocytes/macrophages release many pro-angiogenic cytokines such as basic fibroblast growth factor (bFGF), VEGF, interleukin-8 (IL-8), substance P, tumor necrosis factor-α (TNF-α), transforming growth factor (TGF)-α and -β, and prostaglandins [Sunderkotter, 1994 #4; Moldovan, 2005 #26] which have action directly or indirectly on promoting endothelial cell proliferation, migration, or tube formation [Shireman, 2007 #23; Sunderkotter, 1994 #4]. Although as well as pro-angiogenic factors, monocytes/macrophages are also able to release anti-angiogenic cytokines such as thrombospodin 1, interferon-α and -γ [Sunderkotter, 1994 #4], their production of inhibitory cytokines is regulated by pro-angiogenic factors. For example, such as IL-12 is inhibited by increasing Ang-2 [Murdoch, 2007 #59].

Third, monocytes/macrophages may differentiate into endothelial cells, which helps directly on vessel wall production [Moldovan, 2005 #26; Moldovan, 2000 #28; Anghelina, 2006 #27]. With specific pro-angiogenic factor stimulation, monocytes/macrophage progenitors can transdifferentiate into endothelial-like cells, which are directly incorporated into new blood vessels [Schmeisser, 2003 #30; Schmeisser, 2002 #29; Shireman, 2007 #23; Hoenig, 2008 #31].

Fourth, with exposure to VEGF or hypoxia, endothelial cells produce MCP-1 [Marumo, 1999 #34; Lakshminarayanan, 2001 #35] as well as VEGF [Moldovan, 2005 #26] and angiopoietin [Murdoch, 2007 #59], all of which activate and attract monocytes/macrophages [Shireman, 2007 #23]. In reverse, monocytes/macrophages not only up-regulate Tie-2 (angiopoietin receptor) [Murdoch, 2007 #59], but also secrete MCP-1 and VEGF when they are activated by hypoxia, which has influence on endothelial cells and even themselves by auto- and paracrine actions, and subsequently brings redoubling effect to the angiogenesis process [Ferrara, 2004 #60].

Angiogenesis in Tumor and Chronic Inflammation

For recent decades, there has been accumulating evidence that together with tumor cells themselves, monocytes/macrophages also play a major role in angiogenesis and progression of tumors [Sunderkotter, 1994 #4] as neoplastic tissues exhibited neovascularization only with macrophages [Mostafa, 1980 #64] and monocyte depleted animals showed a significant decrease of tumor angiogenesis [Evans, 1977 #63]. The number of macrophages in tumor tissue is greater than in most normal tissue [Gouon-Evans, 2002 #79]. Rather than proliferation of tissue macrophages themselves, augmented mobilization and differentiation from circulating monocytes more likely result in increased macrophages in tumor tissue [Mantovani, 2002 #15; Schmid, 2007 #13]. The pro-inflammatory cytokines which are induced by tumor cells and central hypoxia, attract monocytes/macrophages to sites of neoplastic necrosis and growth [Pugh-Humphreys, 1992 #44; Coussens, 2002 #78].

Most of all, monocytes/macrophages appear to be recruited to promote neovascularization that is critical to tumor growth and progression. In most tumors, significantly more of the tumor associated macrophages (TAMs) are of the M2 macrophage subpopulation, which potentiate angiogenesis, compared to the M1 subset which kills tumor cells [Sironi, 2006 #17; Mantovani, 2002 #15; Sica, 2006 #16]. M2 TAMs secrete plenty of pro-angiogenic factors, such as VEGF, TNF-α, IL-8, TGF-β and bFGF [Mantovani, 2002 #15; Sica, 2006 #16; Murdoch, 2004 #1; Nozawa, 2006 #18; Schmid, 2007 #13; Mantovani, 2004 #67], and a broad range of proteolytic enzymes [Nozawa, 2006 #18], which can break down the extracellular matrix and in turn, lead to endothelial cell migration for angiogenesis [Moldovan, 2005 #26; Schmid, 2007 #13]. Of important, significant correlations between TAM and vascular densities, have been observed in colon cancer [Oosterling, 2005 #10], breast cancer [Leek, 2002 #12], and pancreatic cancer [Esposito, 2004 #11], which suggest that TAMs potentiate tumor angiogenesis [Schmid, 2007 #13]. Besides, strong TAM recruitment is significantly related with poor prognosis in some tumor types [Leek, 2002 #12; Oosterling, 2005 #10].

Angiogenesis also contributes to chronic inflammatory pathology. The chronic inflammatory status is able to be maintained by virtue of new vessel formation, which continuously delivers inflammatory cells and supplies oxygen and nutrients to the area of inflammation [Jackson, 1997 #37]. Mechanisms and characteristics of neovascularization related to chronic inflammation are no different than angiogenesis induced by ischemia or tumor. Most cytokines and growth factors known to regulate angiogenesis can be produced by monocytes/macrophages [Sunderkotter, 1994 #4]. During pannus formation in rheumatoid arthritis and atheromatous plaque formation in atherosclerosis, the proliferating inflamed tissue contains a number of inflammatory cells, especially monocytes/macrophages, newly forming vessels, and derived inflammatory mediators [Jackson, 1997 #37]. The end result is that increased monocytes/macrophages can be observed at most inflammatory areas where angiogenesis is occurring in an abnormal environment, including pathologic conditions such as ischemia, tumor and chronic inflammatory disease as well as wound healing [Wagner, 2008 #38; Jackson, 1997 #37; Sunderkotter, 1994 #4; Hunt, 1984 #39].

Monocytes Versus Stem Cells for Transplantation

A number of studies have been performed to explore the therapeutic potential of monocytes/macrophages for arteriogenesis and/or angiogenesis primarily in ischemic disease models [Buschmann, 2001 #42; Heil, 2002 #43; Herold, 2004 #33; Ito, 1997 #45; Hirose, 2008 #65]. For arteriogenesis and angiogenesis, monocyte may be novel and fascinating as a target cell for cell-based therapy towards promotion of collateral vessel growth followed by tissue regeneration, which can attenuate local tissue ischemia and improve clinical outcomes [Sasayama, 1992 #40; Krupinski, 1994 #54]. Neovascularization from endogenous monocytes can be induced directly by an infusion of MCP-1 [Ito, 1997 #45], or granulocyte-macrophage colony stimulating factor (GM-CSF) [Buschmann, 2001 #42], or indirectly through a rebound effect after administration of 5-fluorouracil [Heil, 2002 #43]; all of these materials can promote homing to and accumulation around collateral arteries, or proliferation of endogenous monocytes.

In addition, neovascularization can be achieved by the transplantation of exogenous autologous or allogeneic monocytes with or without ex vivo engineering. With developing an effective method for isolation of monocytes from peripheral blood [Herold, 2006 #46; Gonzalez-Barderas, 2004 #47; de Almeida, 2000 #48; Repnik, 2003 #49], an adequate autologous monocyte stock can be collected. Although peripheral blood yields a finite number of monocyte, monocyte stock can reach to proper cell amount for future using through repeated harvesting of autologous monocytes from the subject's peripheral blood by leucapharesis [Herold, 2006 #46]. The advance of ex vivo tissue engineering leads to new strategy using monocytes as vehicles for therapeutic gene transfection, for example, delivery of GM-CSF to promote neovascularization [Herold, 2004 #33] as well as direct effectors for cell transplantation. This technical development from cell isolation to application should make monocytes more promising for regenerative medicine, especially in terms of augmentation of arteriogenesis and angiogenesis.

There may be several advantages of monocyte transplantation (Table 1) compared to stem cells. First, unlike progenitor/stem cells, they do not have the ability to self-renew and proliferate, thus decreasing the potential for tumorogenesis from the cell transplant. Second, they cannot differentiate into other cell lineages, which could exert undesired effects in specific tissues if they are transplanted into or migrate into them. Third, unlike embryonic and fetal tissues, they are free from ethical and moral issues for procurement and transplantation because they can be easily collected from perinatal and adult peripheral blood or bone marrow. Fourth, monocyte transplantation can avoid an immune reaction such as graft-versus-host disease (GvHD), which often happens after allogenic leukocyte transfusion or BM transplantation in human leukocyte antigen (HLA) mis-matched host. GvHD is an immune reaction which result from activation of T-cells in the graft (donor cells) after detecting host tissues (recipient cells) as antigenically different [Brichard, 2001 #75]. The activated donor T-cells produce an abundance of cytotoxic and inflammatory cytokines and attack the host tissues. With respect to GvHD, regardless of HLA matching, transplantation of monocyte fraction alone should be safe to a greater degree than that of mononuclear fraction of BM or GM-CSF mobilized peripheral blood, which is sure to include lymphocytes. Finally, monocytes/macrophages can secrete a number of cytokines, growth factors and trophic materials which may directly promote other tissue regeneration as well as angiogenesis [Sunderkotter, 1994 #4]. For instance, VEGF has been known to be able to stimulate neurogenesis [Jin, 2002 #55; Teng, 2008 #61].

Monocytes from Umbilical Cord Blood

Monocytes constitute ~5-10% of peripheral blood leukocytes in humans [Gordon, 2005 #72; Mielcarek, 1997 #74], whereas these cells comprise 2% of BM mononuclear cells [Mielcarek, 1997 #74]. By contrast, no difference in monocyte content between umbilical cord blood (UCB) and adult peripheral blood has been reported [Sorg, 2001 #73; Mills, 1996 #71]. Therefore, BM and UCB, as well as peripheral blood can be potential candidates as a source of autologous or allogeneic monocytes/macrophages. In fact, BM and UCB are the current gold standard sources of hematopoietic progenitor cells used to reconstitute blood lineages after myeloablative therapy in malignant and nonmalignant blood disease. However, the potential of their stem cell population for cell-based therapy has also been demonstrated in other degenerative disorders, especially ischemic disease. There is accumulating evidence that delivery of bone marrow stem cells or umbilical cord blood stem cells to areas of ischemia by direct local transplantation or injection into blood, can improve the pathological lesion and functional impairment [Henning, 2007 #70; Chen, 2003 #51; Willing, 2003 #52; Newcomb, 2007 #26; Chang, 2007 #143]. This improvement has been thought to result in part from angiogenesis induced by stem cells in the ischemic and/or peri-ischemic core [Chen, 2003 #51; Taguchi, 2004 #53; Chang, 2007 #143] even though the mechanisms by which these cells exert their angiogenic effects are not completely understood.

Essentially, monocytes in UCB are unique compared to those originating in adult BM and peripheral blood [Newcomb, 2007 #26]. Only adult monocytes are activated by hepatocyte growth factor, which is essential for normal monocyte functions such as antigen presentation [Jiang, 2001 #154]. The UCB monocytes express less human leukocyte antigen-DR than adult cells so their cytotoxic capacity is lower [Theilgaard-Monch, 2001 #155]. Furthermore, UCB monocytes do not differentiate into mature dendritic cells to the same extent as mature monocytes even with stimulation by IL-4 and GM-CSF [Liu, 2001 #66]; dendritic cells play a major role in activation of naïve T cells. Secretory function is also different between UCB monocytes and adult blood monocytes. Less secretion of IL-1β and TNF-α, both of which stimulate inflammation as well as play a major role in immune reactions such as GvHD [Hill, 1997 #76], from UCB monocytes after exposure to recombinant interferon-γ is most likely related to differences in the expression of monocytes antigens such as CD64, CD14, CD33 and CD45RO with adult blood monocytes [Brichard, 2001 #75]. $CD14^+$ monocytes/macrophages in uterine decidual tissues and blood of normal pregnant women are predominantly M2 subset, which modulates maternal-fetal immune reaction and promotes tissue remodeling and angiogenesis to maintain successful pregnancy [Gustafsson, 2008 #69]. These findings suggest that most UCB monocytes may also become M2 polarized macrophages which are less inflammatory and more angiogenic because decidual macrophages probably are differentiated from UCB monocytes in part.

The immaturity of immune and inflammation stimulatory function in UCB monocytes may contribute to a lower incidence of immune rejection including GvHD and/or inhibition of deleterious inflammatory reaction after transplantation even though they are from an allogeneic source. Although, transplantation of monocytes from autologous BM or peripheral blood can avoid immune rejection and GvHD, BM harvesting itself needs additional time, cost, and physical burden to the patients. Repeated monocyte harvesting and isolation from the patient's own peripheral blood also necessitates extra time and cost. By contrast, in terms of target for cell-based therapy, one of the largest advantages of UCB monocytes compared to adult autologous monocytes is rapid availability. For example, in stroke patients, "proper timing" is critical and it may not be feasible to recover, maneuver, and process quality handle cells, in a current good manufacturing practices (cGMP) condition from the patient within the therapeutic window. As far as feasibility and safety is concerned, UCB monocytes are the most promising allogenic cells that can be manipulated completely in advance without harm to donor or recipient before transplantation even if the cells are immunologically mismatched to those of the recipient. Table 2 shows the advantages of UCB monocytes for cell-based therapy.

This superiority of UCB monocytes over BM and peripheral blood should lead to more brisk exploration of their promising role for cell-based therapy. Recently, our group showed that transplantation of human UCB cells from which the monocyte subpopulation ($CD14^+$) was depleted failed to improve neurological outcome to the same extent as transplantation of the other UCB cells (T-cell depleted, B-cell depleted, $CD133^+$ depleted, and whole mononuclear fraction) in the middle cerebral artery occlusion rat model (Womble, et al., 2008). In regard to angiogenesis, these findings suggest that transplantation of monocyte-depleted human UCB could not induce angiogenesis properly, and in turn, did not improve neurological dysfunction. At least, the monocyte subpopulation of UCB should be critical to UCB-induced recovery following stroke.

In addition, we also demonstrated that locomotor dysfunction and memory were improved after intravenous transplantation of monocyte/macrophages from human UCB in a Sanfilippo syndrome type B (MPS III B) mouse model (Garbuzova-Davis, et al., 2008). In MPS III B, a deficiency of the α-N-acetylglucosaminidase (Naglu) enzyme leads to accumulation of heparan sulfate (HS), a glycosaminoglycan within cells and finally draws to progressive cerebral and systemic organ abnormalities. Although glycosaminoglycans are known as extracellular matrix molecules that have influence on the phagocytic ability of macrophages, the function of monocytes/macrophages in a pathological HS-rich condition such as Sanfilippo syndrome is unclear. In this study, as well as neurological improvement, histopathological study showed that the number of microglia (macrophage in brain) increased in all hippocampal areas of Naglu mutant mice treated with monocytes and HS levels reduced in the livers of treated mice. Furthermore, urinary distention, usually a significant problem in aged afflicted mice, was also improved in treated mice. These findings suggest that administration of human UCB monocytes/macrophages should benefit mice modeling MPS III B, probably owing to the influence from transplanted cells on mechanisms of phagocytosis in the HS-rich environment of this disease (Garbuzova-Davis, et al., 2008).

Of course, the capability of monocytes for cell transplantation has to be carefully evaluated before clinical therapeutic application, as their specific role and function in inflammation and immune modulation has still not been fully understood. Their deleterious potential in tumor vascularization, diabetic retinopathy, arthritic pannus, and atherosclerotic plaque development also may need serious investigation [Herold, 2006 #46]. However, these hazardous side effects can be prevented by way of careful evaluation as to whether the proposed recipient has pre-existing malignancy, uncontrolled diabetes, arthritis, atherosclerosis or not. If during pre-treatment evaluation, it is confirmed that the patients have a pre-existing disease which may be exacerbated by monocyte transplantation, they would be excluded before cell transplantation. This is unlikely since monocyte-related complications, to the best of our knowledge, have not been reported, such as pre-existing tumor or chronic inflammatory disease progression, after BM or UCB transplantation in patients with hematologic malignant or nonmalignant diseases even though monocytes comprise a considerable portion of BM and UCB.

By contrast, use of UCB monocytes may prevent probable harmful effects or exert anti-inflammatory effects. There has been accumulating evidence that UCB mononuclear cells provide anti-inflammatory reaction in several disease conditions. Previously, we demonstrated that the transplantation of mononuclear human UCB cells significantly decreased the number of $CD45^+/CD11b^+$ (microglia/macrophage) and $CD45^+/B220^+$ (B-cell) cells in the brain of rats with middle cerebral artery occlusion [Vendrame, 2005 #106]. In addition, UCB transplantation decreased the pro-inflammatory cytokines such as TNF-α and IL-1β [Vendrame, 2005 #106]. Recently, we also revealed that transplantation of human UCB mononuclear cells via intravenous injection in older rats can significantly reduce the number of activated microglia, and increase neurogenesis [Bachstetter, 2008 #5]. Chronic microgliosis reflects chronic inflammatory reaction in brain tissue, and is involved in neural structure damage in ischemic injury as well as in other neurodegenerative diseases such as Parkinson's and Alzheimer's disease [Streit, 1999 #9]. Therefore, this finding suggests that UCB mononuclear cells can ameliorate the hostile environment of the aged hippocampus by way of anti-inflammatory reaction, and subsequently regenerate potential of the aged neural stem/progenitor cells. On the basis of above studies, monocyte fraction which comprises UCB mononuclear cells considerably, should have the potential of anti-inflammatory reaction which may be partially responsible for the functional improvements seen in animal models of injury, including stroke.

In conclusion, monocytes/macrophages may provide a promising alternative to stem cell transplantation for therapeutic purposes with the ability to promote arteriogenesis and angiogenesis in varied diseases. These monocytes should be the first candidate out of several due to their outstanding feasibility, safety, and multiple functions such as anti-inflammatory reaction as well as angiogenesis.

The invention has been described in an illustrative manner, and it is to be understood the terminology used is intended to be in the nature of description rather than of limitation. Obviously, many modifications and variations of the present invention are possible in light of the above teachings and one of ordinary skill in the art, in light of this teaching, can generate additional embodiments and modifications without departing from the spirit of or exceeding the scope of the claimed invention. Therefore, it is to be understood that within the scope of the appended claims, the invention may be practiced otherwise than as specifically described. Accordingly, it is to be understood that the drawings and descriptions herein are proffered by way of example to facilitate comprehension of the invention and should not be construed to limit the scope thereof.

We claim:

1. A method of treatment of ischemia in a subject comprising injecting a therapeutic cell population into the ischemic tissue of the subject, wherein the therapeutic cell population comprises a mononuclear cell population enriched for monocyte lineage cells and wherein the monocyte lineage cells comprise promonocytes.

2. The method of claim 1 wherein the ischemia is cardiac ischemia and the ischemic tissue is ischemic myocardium.

3. The method of claim 2 wherein the therapeutic cell population injected into the myocardium includes at least $10^7$ monocyte lineage cells.

4. The method of claim 2 wherein the therapeutic cell population is injected into the myocardium through at least two separate injections, at least three separate injections, at least four separate injections, at least five separate injections, at least ten separate injections, at least twenty separate injections, at least thirty separate injections, or at least forty separate injections.

5. The method of claim 1 wherein an injection is between 0.05 ml and 0.3 ml.

6. The method of claim 5 wherein the injection is about 0.2 ml.

7. The method of claim 1 wherein the therapeutic cell population is autologous to the subject.

8. The method of claim 1 wherein the therapeutic cell population is allogeneic to the subject.

9. The method of claim 1 wherein the therapeutic cell population is a mononuclear cell population enriched for monocyte lineage cells and wherein the monocyte lineage cells comprise promonocytes.

10. The method of claim 1, wherein the mononuclear cell population was obtained from bone marrow, cord blood or mobilized peripheral blood.

11. The method of claim 1, wherein the mononuclear cell population was obtained from bone marrow.

12. The method of claim 1, wherein the enrichment for monocyte lineage cells comprised isolating the therapeutic cells from a sample using a method that enriches monocyte lineage cells; culturing the therapeutic cell population under conditions that enriches monocyte lineage cells; and/or adding monocyte lineage cells to the therapeutic cell population.

13. A method of improving perfusion in a subject comprising injecting a therapeutic cell population into a tissue of the subject in need of improved perfusion, wherein the therapeutic cell population comprises a mononuclear cell population enriched for monocyte lineage cells and wherein the monocyte lineage cells comprise promonocytes.

14. The method of claim 13 wherein the perfusion is cardiac perfusion and the tissue is myocardium.

15. The method of claim 13, wherein the mononuclear cell population was obtained from bone marrow, cord blood or mobilized peripheral blood.

16. The method of claim 13, wherein the mononuclear cell population was obtained from bone marrow.

17. The method of claim 13, wherein the enrichment for monocyte lineage cells comprised isolating the therapeutic cells from a sample using a method that enriches monocyte lineage cells; culturing the therapeutic cell population under conditions that enriches monocyte lineage cells; and/or adding monocyte lineage cells to the therapeutic cell population.

* * * * *

UNITED STATES PATENT AND TRADEMARK OFFICE
CERTIFICATE OF CORRECTION

| | | |
|---|---|---|
| PATENT NO. | : 8,784,802 B2 | Page 1 of 1 |
| APPLICATION NO. | : 13/063456 | |
| DATED | : July 22, 2014 | |
| INVENTOR(S) | : Sanberg et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 365 days.

Signed and Sealed this
Seventeenth Day of November, 2015

Michelle K. Lee
*Director of the United States Patent and Trademark Office*